Figure 3:
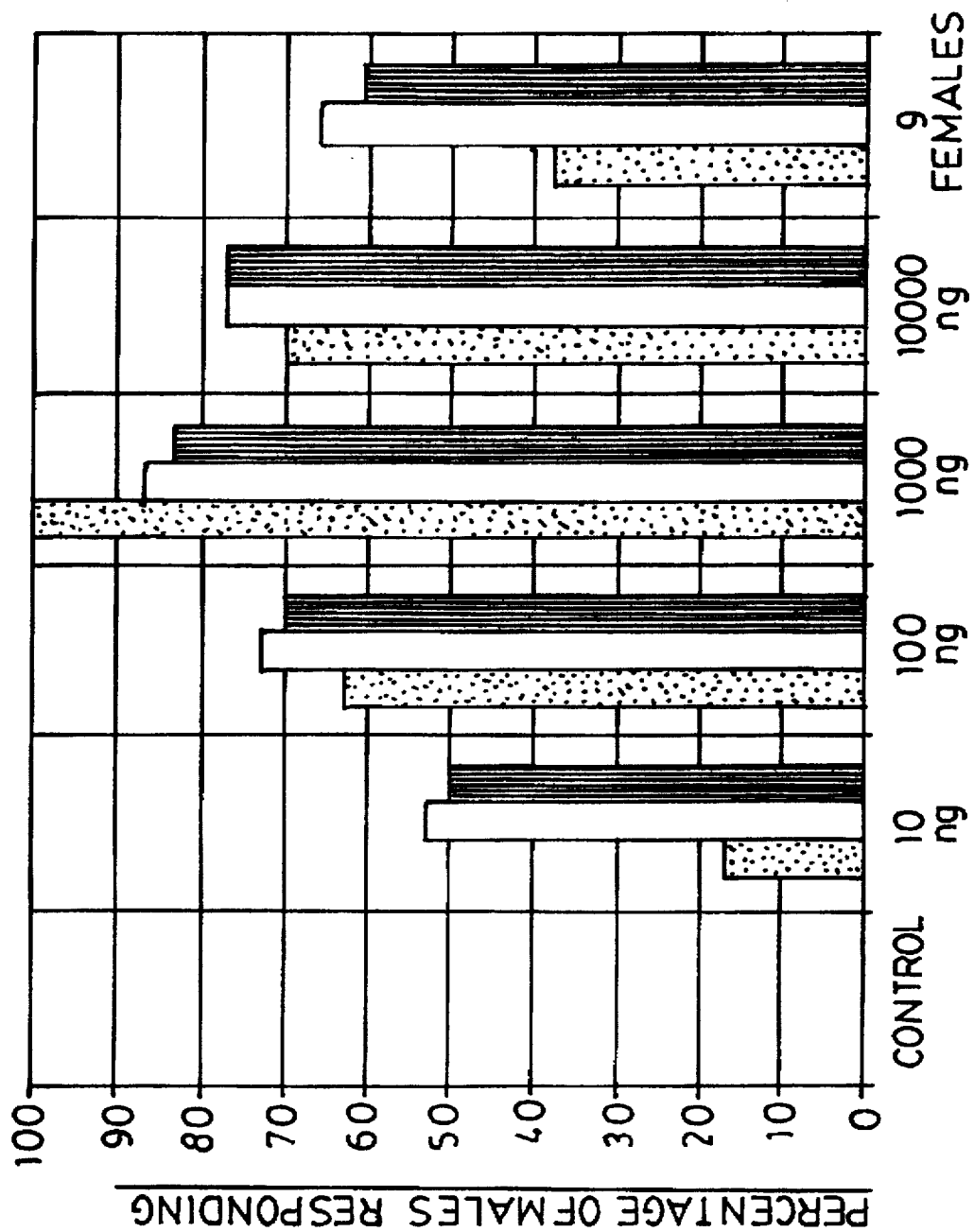
Figure 4A:
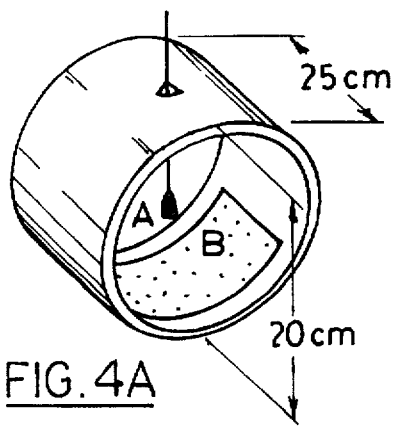
Figure 4B:
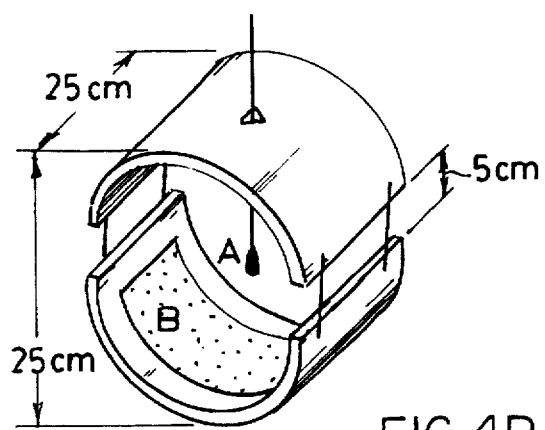
Figure 4C:
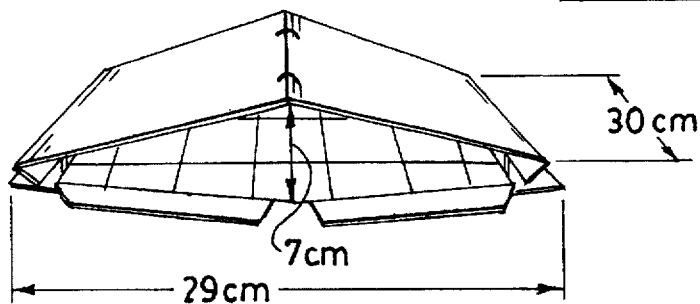
Figure 4D:
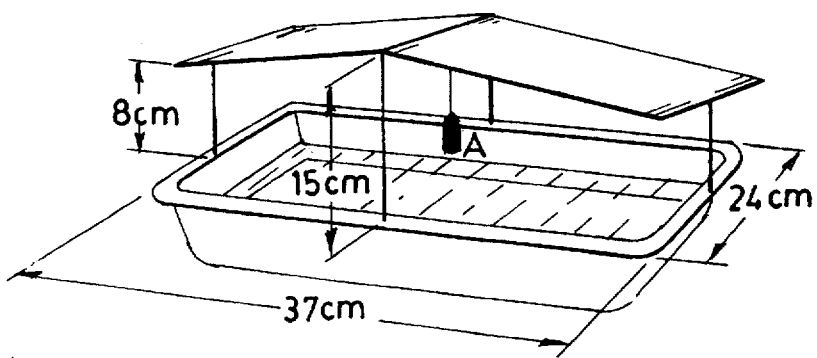
Figure 4E:
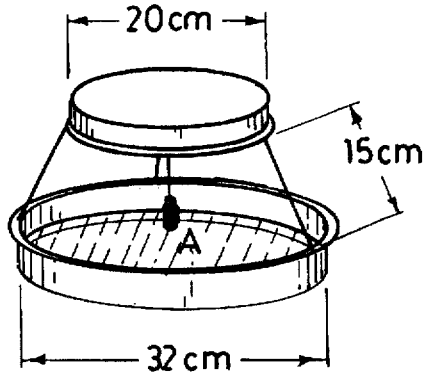

United States Patent [19]

Attygalle et al.

[11] Patent Number: 5,728,376
[45] Date of Patent: Mar. 17, 1998

[54] TETRADECATRIENYL AND TETRADECADIENYL ACETATES AND THEIR USE AS SEX ATTRACTANTS FOR TOMATO PESTS

[75] Inventors: Athula B. Attygalle, Ithaca, N.Y.; Gulab N. Jham, Viçosa, Brazil; Aleš Svatoš, Prague, Czech Rep.; Rosa T.S. Frighetto, Campinas, Brazil

[73] Assignee: Cornell Research Foundation, Inc., Ithaca, N.Y.

[21] Appl. No.: 428,406

[22] Filed: Apr. 25, 1995

[51] Int. Cl.$^6$ .................. A01N 31/02; C07C 33/02; C07C 33/048; C07C 21/02
[52] U.S. Cl. .................. 424/84; 560/261; 568/849; 568/850; 568/873; 568/903; 43/132.1
[58] Field of Search .................. 424/405, 84; 560/261; 568/849, 850, 873, 903

[56] References Cited

U.S. PATENT DOCUMENTS

| | | | |
|---|---|---|---|
| 3,980,771 | 9/1976 | Meijer et al. | 424/84 |
| 3,991,125 | 11/1976 | Labovitz et al. | 424/84 |
| 4,147,771 | 4/1979 | Struble et al. | 424/84 |
| 4,189,614 | 2/1980 | Samain | 568/908 |
| 4,284,622 | 8/1981 | Underhill et al. | 424/84 |
| 4,296,042 | 10/1981 | Muchowski et al. | 260/345.9 R |
| 4,609,498 | 9/1986 | Banasiak et al. | 260/410.9 R |
| 4,654,461 | 3/1987 | Drake et al. | 585/600 |
| 4,834,745 | 5/1989 | Ogawa et al. | 424/409 |
| 4,844,916 | 7/1989 | Ogawa et al. | 424/409 |
| 5,236,715 | 8/1993 | McDonough et al. | 424/84 |
| 5,252,326 | 10/1993 | Novotny et al. | 424/54 |
| 5,380,524 | 1/1995 | McDonough et al. | 424/84 |

OTHER PUBLICATIONS

Attygalle, "Gas phase infrared spectroscopy in characterization of unsaturated natural products," *Pure & Appl. Chem.*, 66(10/11):2323–2326 (1994).

Attygalle, et al., "Gas-Phase Infrared Spectroscopy for Determination of Double Bond Configuation of Monounsaturated Compounds," *Analytical Chemistry*, 66(10):1696–1703 (1994).

Nesbitt, et al., "Identification of components of the female sex pheromone of the potato tuber moth, *Scrobipalpopsis solanivora*," *Entomol. exp. appl.* 38:81–85(1985).

Persoons, et al., "Sex pheromone of the potato tuberworm moth, *Phthorimaea operculella*: isolation, identification and field evaluation," *Ent. exp. & appl.*, 20:289–300 (1976).

Renou, et al., "L'acétoxy-1 dodécène 3E, composant principal de la phéromone sexuelle de la betterave: *Scrobipalpa ocellatella* Boyd. (Lépidoptère Gelechiidae)," *Z. ang. Ent.*, 90:275–279 (1980).

Roelofs, et al., "Lepidopterous sex attractants discovered by field screening tests" *J. Econ. Entomol.*, 63(5):969–974 (1970).

Svatoš, et al., "Synthesis of deuterium labeled polyunsaturated fatty acids," *Tetrahedron Letters*, 35(51):9497–9500 (1994).

*Primary Examiner*—Edward J. Webman
*Attorney, Agent, or Firm*—Nixon, Hargrave, Devans & Doyle

[57] ABSTRACT

The present invention is directed to compounds useful as moth attractants and to methods for controlling populations of the tomato moth *Scrobipalpuloides absoluta* with these compounds. The compounds are 3,8,11-tetradecatrienyl acetates, 3,8-tetradecadienyl acetates, 3,11-tetradecadienyl acetates, and 8,11-tetradecadienyl acetates. Preferred compounds are (3E,8Z,11Z)-3,8,11-tetradecatrienyl acetate, (3E,8Z)-3,8-tetradecadienyl acetate, (3E,11Z)-3,11- tetradecadienyl acetate, and (8Z,11Z)-8-11-tetradecadienyl acetate. The compounds can be used as an attractant in moth traps comprising, in addition to the compounds, a moth restraint. Alternatively, the compounds of the present invention can be combined with a biocontrol agent or an insecticide for use as a moth control composition. Synthesis of (3E,8Z,11Z)-3,8, 11-tetradecatrienyl acetate is described.

62 Claims, 5 Drawing Sheets

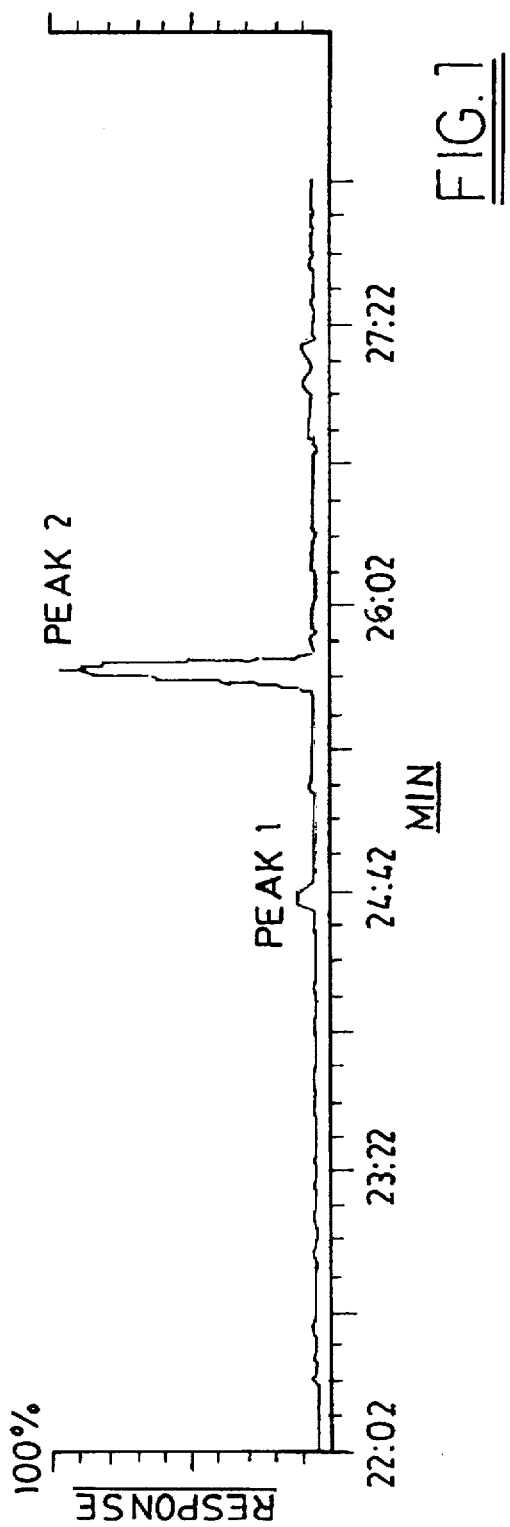
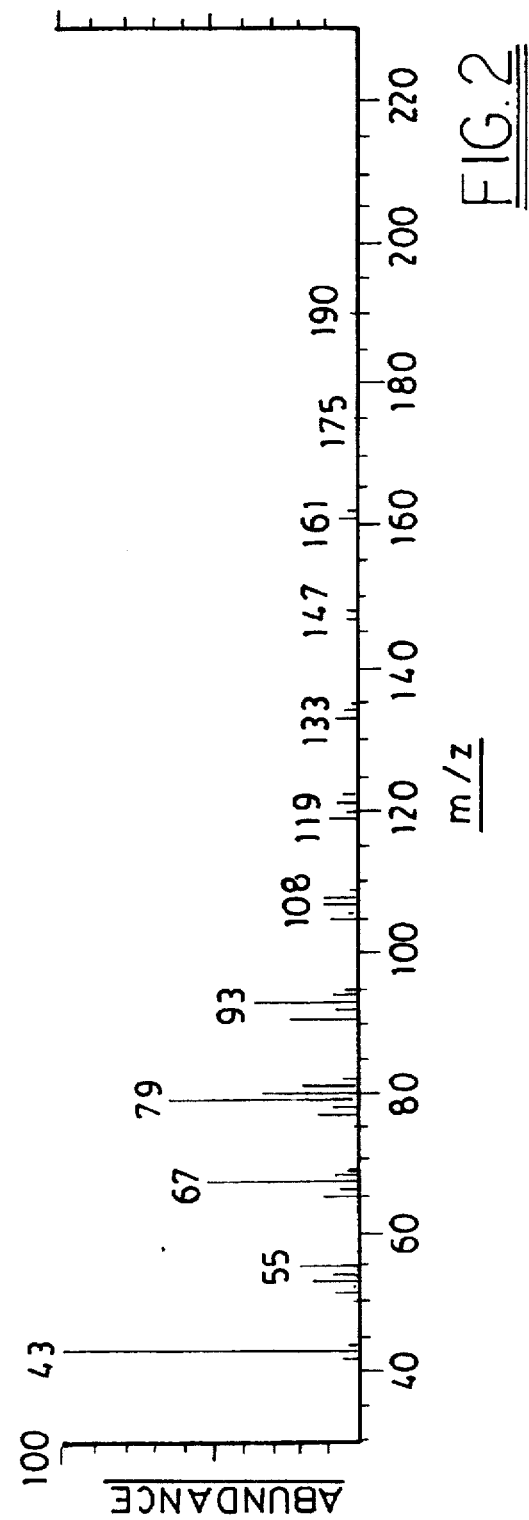

TETRADECATRIENYL AND TETRADECADIENYL ACETATES AND THEIR USE AS SEX ATTRACTANTS FOR TOMATO PESTS

This invention was made through the support of the National Science Foundation (Grant INT9202380). The Federal Government may retain certain rights in the invention.

FIELD OF THE INVENTION

This invention relates to moth attractants and to methods for synthesizing and using these attractants.

BACKGROUND OF THE INVENTION

Tomato (*Lycopersicon esculentum*) is an economically important plant which is cultivated extensively all over the world. However, tomato is extremely susceptible to insect attack by *Scrobipalpuloides absoluta* (Lepidoptera: Gelechiide) (Gallo et al. in *Manual de Entomologica Agricola*, 2nd ed., Ceres, ed., Sao Paulo, Brazil, 649 (1988)). In the past, the pest has been known as *Scrobipalpa absoluta* and *Scrobipalpulpa absoluta* (Meyrick). It is known locally as "traça-do-tomateiro" in Brazil and as "polilla del tomate" in other Latin American countries. The pest is particularly active in Latin America where it causes severe damage in all tomato growing countries including Venezuela, Columbia, Chile, Ecuador, Bolivia, Peru and Uruguay. Brazil, which has about 55,000 acres under tomato cultivation, has been particularly affected. Since 1981, when Moreira et al., "Ocorrencia de *Scrobipalpula absoluta* danificando tomateiro rasteiro em Jaboticabal," S.D. in *Congresso Brasileiro de Entomologic Fortaleza Ce*, 58 (1981), first reported the pest in Brazil in the state of Sao Paulo, infestation has spread to other states, such as Minas Gerais, Salvador, Espirito Santo and Rio de Janeiro. Losses of up to 100% have been described.

The need to suppress *Scrobipalpuloides absoluta* populations ("*S. absoluta*") has resulted in the application of large amounts of conventional, broad-based insecticides by blanket spraying. The method, however, has serious limitations. It is now well established that continuous or repeated pesticide use results in the emergence of insect strains which resist the chemicals being applied, making subsequent insect control more difficult. Furthermore, application of broad-based pesticides upsets delicate natural balances by eliminating non-targeted species, including natural predators of the pest and pollinators. The use of insecticides also adversely impacts the farmers, both economically and medically. The cost of broad-based insecticides and the cost of their application place a heavy financial burden on poor farmers. The use of pesticides also subjects farmers and other inhabitants living near tomato fields to the hazards of exposure. This exposure is particularly severe in Latin America, where farmers' residences are typically in close proximity to their tomato fields. Moreover, it is generally known that some pesticide residues enter and move along the food web, thus exposing virtually all living organisms to these hazardous chemicals. The drawbacks associated with blanket spraying are exacerbated by the fact that such spraying must be repeated at regular intervals, typically weekly, during the growing season because the insecticide is effective only against adult moths. Moths in the larval stage, having burrowed inside the leaves, stems, and fruits, remain unexposed and unaffected. Accordingly, there is a continuing need for the development of safe, effective, and environmentally compatible moth control techniques.

In recent years, compounds known as pheromones have been recognized as useful components of successful pest control programs. A pheromone is generally defined as a chemical substance secreted by living organisms, including insects, to convey information or produce a specific response in other individuals of the same species. Sex pheromones may be a single compound but typically take the form of a complex, volatile blend of compounds which is, for example, secreted during the mating cycle. As such, sex pheromones often serve as "attractants"; that is, the pheromone attracts insects of the same species to the location of the pheromone emission.

Attractants for many species of moth have been identified. For example, Persoons et al., "Sex pheromone of the potato tuberworm moth, *Phthorimaea operculella*: isolation, identification and field evaluation," *Entomol. Exp. Appl.*, 20:289–300 (1976), disclose the use of (4E,7Z,10Z)-4,7,10-tridecatrienyl acetate, together with the corresponding diene, (4E,7Z)-4,7-tridecatrienyl acetate, as a sex attractant for *Phthorimaea operculella*. Nesbitt et al., "Identification of components of the female sex pheromone of the potato tuber moth, *Scrobipalpopsis solanivora*," *Entomol. Exp. Appl.*, 38:81–85 (1985), have identified (E)-3-decen-1-yl acetate as a pheromone constituent of the potato tuber moth, *Scrobipalposis solanivera* Povolny. Pheromones for some insects from the Scrobipalpa family have also been identified. These include: (E)-3-tridecen-1-yl acetate for the tobacco stem borer moth, *Scrobipalpa heliopa* (Lower) (Baker et al., "Sex pheromone of tobacco stem borer *Scrobipalpa heliopa* (Lower) (Lepidoptera: Gelechiidae)," *J. Chem Ecol.*, 11:989–998 (1985)) and (E)-3-dodecen-1-yl acetate for the sugar beet moth, *Scrobipalpa ocellatella* Boyd (Renou et al., "L'acétoxy-1 dodécène 3E, composant principal de la phéromone sexuelle de la teigne de la betterave: *Scrobipalpa ocellatella* Boyd. (Lépidoptère Gelechiidae)," *Z. ang. Entomol.*, 90:275–289 (1980)).

No attractant has yet been identified for the tomato moth, *Scrobipalpuloides absoluta*, and, therefore, blanket spraying of broad-based insecticides, with all its associated limitations and adverse impacts, remains the dominant control method. For these and other reasons, a need exists for pheromone attractants for *S. absoluta* and methods of employing this attractant to control *S. absoluta* populations.

SUMMARY OF INVENTION

The present invention relates to attractants for moths as well as to the synthesis and use of these compounds. One aspect of the present invention relates to an isolated 3,8,11-tetradecatrienyl acetate.

Another aspect of the present invention relates to an isolated tetradecadienyl acetate. The tetradecadienyl acetate is selected from the group consisting of a 3,8-tetradecadienyl acetate, a 3,11-tetradecadienyl acetate, and an 8,11-tetradecadienyl acetate.

The present invention also provides an attractant blend comprising two or more compounds. The compounds are selected from the group consisting of a 3,8-tetradecadienyl acetate, a 3,11-tetradecadienyl acetate, an 8,11-tetradecadienyl acetate, and a 3,8,11-tetradecatrienyl acetate.

The present invention further provides a moth trap comprising a restraining member and a moth attractant used in conjunction with the moth restraining member. The moth attractant is selected from the group consisting of a 3,8-tetradecadienyl acetate, a 3,11-tetradecadienyl acetate, an 8,11-tetradecadienyl acetate, a 3,8,11-tetradecatrienyl acetate, and mixtures thereof.

The invention further provides a moth control composition comprising a moth attractant and either an insecticide or a biocontrol agent. In each of these moth control compositions, the moth attractant is selected from the group consisting of a 3,8-tetradecadienyl acetate, a 3,11-tetradecadienyl acetate, an 8,11-tetradecadienyl acetate, a 3,8,11-tetradecatrienyl acetate, and mixtures thereof.

A method for attracting moths to a particular location is also provided in accordance with the present invention. Moths are attracted by providing at the particular location about 10 picograms to about 10 milligrams of a moth attractant. The moth attractant is selected from the group consisting of a 3,8-tetradecadienyl acetate, a 3,11-tetradecadienyl acetate, an 8,11-tetradecadienyl acetate, a 3,8,11-tetradecatrienyl acetate, and mixtures thereof.

The present invention further provides a method for controlling a population of moths. According to this method of the subject invention, moths are attracted to a particular location with about 10 picograms to about 10 milligrams of a moth attractant selected from the group consisting of a 3,8-tetradecadienyl acetate, a 3,11-tetradecadienyl acetate, an 8,11-tetradecadienyl acetate, a 3,8,11-tetradecatrienyl acetate, and mixtures thereof. Proximate to this particular location, the moths are exposed to an agent which impairs the moths' ability to mate. Suitable agents include, for example, a restraining device, an insecticide, or a biocontrol agent.

The present invention also provides a method of disrupting mating of moths in a particular area. The method includes providing in the particular area a quantity of an attractant selected from the group consisting of a 3,8-tetradecadienyl acetate, a 3,11-tetradecadienyl acetate, an 8,11-tetradecadienyl acetate, a 3,8,11-tetradecatrienyl acetate, and mixtures thereof. The quantity provided is above that emanating from moths and sufficient to prevent pheromone communication.

The invention also relates to a method of synthesizing (3E,8Z,11Z)-3,8,11-tetradecatrienyl acetate. The method involves providing trienyl alcohol having the formula:

 [II]

and acetylating the alcohol.

Another aspect of the present invention pertains to a series of compounds from which (3E,8Z,11Z)-3,8,11-tetradecatrienyl acetate can be prepared. One such compound is a trienyl alcohol having the formula:

 [II]

Another such compound is a dieneynyl alcohol having the formula:

The invention also pertains to a protected dieneynyl alcohol having the formula:

wherein Y is an alcohol protecting group, and a dienyl halide having the formula:

wherein X is a halogen.

The tetradecadienyl and tetradecatrienyl acetates of the present invention are effective and useful moth attractants. They are particularly well suited for attracting moths of the *Scrobipalpuloides absoluta* species. These attractants and the methods of using them provide a biorational alternative to blanket application of broad-based pesticides for combatting *S. absoluta* infestation. Reducing pesticide use benefits the environment, contributes to the conservation of biodiversity of species, and decreases indiscriminate elimination of non-targeted predators of the moth and pollinators. Moreover, reduced dependence on costly pesticides provides a direct economic benefit to farmers plagued by *S. absoluta*.

BRIEF DESCRIPTION OF THE DRAWINGS

FIG. 1 is a section of the reconstructed gas chromatogram obtained from the volatiles present in a female pheromone gland extract of *S. absoluta* (30 m×0.22 mm fused-silica capillary column coated with FFAP stationary phase; temperature program: 40° C. for 4 min, 6° C./min to 190° C.).

FIG. 2 is an electron-ionization mass spectrum (70 eV) of the major female sex pheromone component of *S. absoluta.*

FIG. 3 is a bar graph depicting the percentage of male moths responding in a wind-tunnel behavioral bioassay. Stippled, open, and black bars represent wing fanning, oriented flight, and landing-at-the-source behavior, respectively. Behavior of 30 males were observed for each test stimulus. Hexane (100 µl) and different amounts (10 ng–10 µg) of (3E, 8Z,11Z)-3,8-11-tetradecatrienyl acetate applied to rubber septa, and nine calling females were used as stimuli.

FIG. 4A–4E are drawings of different types of traps.

FIG. 5 is a histogram depicting the average number of males caught per night per trap (N=15) for each of trap designs A–E. Each trap was baited with 1 µg of synthetic (3E,8Z,11Z)-3,8-11-tetradecatrienyl acetate on a rubber dispenser. Vertical bars represent standard deviations.

FIG. 6 is a histogram depicting the average number of male moths caught per trap (N=20) per night by traps baited with 1, 10, or 100 µg of synthetic (3E,8Z,11Z)-3,8-11-tetradecatrienyl acetate on a rubber dispenser, or one one-day-old virgin female. Control baits were treated with 100 µl of distilled hexane. Vertical bars represent standard deviations.

FIG. 7 is a histogram showing the average number of males caught per trap (N=8) per hour by traps baited with 1 µg of synthetic (3E,8Z,11Z)-3,8-11-tetradecatrienyl acetate on a rubber dispenser. Vertical bars represent Standard Deviations.

DETAILED DESCRIPTION OF THE INVENTION

The present invention relates to compounds useful as attractants for moths, the synthesis of these compounds, and the use of these compounds in the management of these pests. One aspect of the present invention relates to an isolated 3,8,11-tetradecatrienyl acetate, having the following general formula:

$CH_3CH_2CH{=}CHCH_2CH{=}CHCH_2CH_2CH_2CH{=}CHCH_2CH_2OC(O)CH_3$

As used herein, an isolated compound is one which is substantially free of the tissue in which it naturally occurs. It is to be understood that the isolated compounds of the present invention are not limited to any particular method of preparation and include, for example, compounds which are prepared by extraction from natural sources as well as those prepared by chemical synthesis. Preferably, the 3,8,11-tetradecatrienyl acetate is substantially pure. In this context, substantially pure means substantially free of compounds other than the particular 3,8,11-tetradecatrienyl acetate. Each of the three double bonds in this compound may independently assume either the trans ("E") or cis ("Z") form. The 3,8,11-tetradecatrienyl acetate can be (3E,8E,11E)-3,8,11-tetradecatrienyl acetate, 3E,8E,11Z)-3,8,11-tetradecatrienyl acetate, 3E,8Z,11E)-3,8,11-tetradecatrienyl acetate, 3Z,8E,11E)-3,8,11-tetradecatrienyl acetate, 3E,8Z,11Z)-3,8,11-tetradecatrienyl acetate, (3Z,8E,11Z)-3,8,11-tetradecatrienyl acetate, (3Z,8Z,11E)-3,8,11-tetradecatrienyl acetate, or (3Z,8Z,11Z)-3,8,11-tetradecatrienyl acetate. Preferably, the 3,8,11-tetradecatrienyl acetate is (3E,8Z,11Z) -3,8,11-tetradecatrienyl acetate, having the formula

  [I]

Another aspect of the present invention relates to an isolated tetradecadienyl acetate. The tetradecadienyl acetate is selected from the group consisting of 3,8-tetradecadienyl acetates, 3,11-tetradecadienyl acetates, and 8,11-tetradecadienyl acetates. Suitable tetradecadienyl acetates include (3E,8E)-3,8 tetradecadienyl acetate, (3E,8Z)-3,8-tetradecadienyl acetate, (3Z,8E)-3,8-tetradecadienyl acetate, (3Z,8Z)-3,8-tetradecadienyl acetate, (3E,11E)-3,11-tetradecadienyl acetate, (3E,11Z)-3,11-tetradecadienyl acetate, (3Z,11E)-3,11-tetradecadienyl acetate, (3Z,11Z)-3,11-tetradecadienyl acetate, (8E,11E)-8,11-tetradecadienyl acetate, (8E,11Z)-8,11-tetradecadienyl acetate, (8Z,11E)-8,11-tetradecadienyl acetate, and (3E,11Z)-8,11-tetradecadienyl acetate. Preferred tetradecadienyl acetates are (3E,8Z)-3,8-tetradecadienyl acetate, (8Z,11Z)-8,11-tetradecadienyl acetate, and (3E,11Z)-3,11-tetradecadedienyl acetate. Respectively, these compounds have the following formulas:

and

preferably, the tetradecadienyl acetate is substantially pore. In this context, substantially pure means substantially free of compounds other than the particular tetradecadienyl acetate.

(3E,8Z,11Z)-3,8,11-tetradecatrienyl acetate can be synthesized by providing the trienyl alcohol having the formula:

  [II]

and acetylating the alcohol. Acetylation can be effected by any of the established techniques, such as, for example, those reviewed in Kemp et al., *Organic Chemistry*, Worth Publishers, New York, 370–378 (1980), which is hereby incorporated by reference. Suitable acetylation methods include acid catalyzed reaction with acetic acid, reaction with acetyl chloride, acid catalyzed transesterification with, for example, an alkyl acetate, and reaction of the alcohol with acetic anhydride. Preferably, acetylation is effected with acetic anhydride in a basic solvent, preferably pyridine.

The trienyl alcohol of Formula (II), used in the above preparation of the acetate of Formula (I), can be prepared by a variety of conventional synthetic routes. Examples of general synthetic strategies of isomerically pure polyeneyl alcohols are provided in Bestmann et al., "Insektenpheromone, Teil 1, Chemische Struktur and Synthese," *Seifen-Öle-Fette-Wachse* 114:612–621 (1988) and Baker et al., "Insect pheromones and related natural products," *Natural Product Reports* 1:299–318 (1984), which are hereby incorporated by reference. Preferably, the trienyl alcohol is prepared by reduction of the corresponding dieneynyl alcohol, having the formula:

  [III]

Choice of reducing agent and reaction conditions are governed by the desirability of preferentially producing the trans isomer and the desirability of minimizing reduction of the resulting double bond or either of the two other double bonds. Suitable reducing reagents include alkali metal in liquid ammonia. The alcohol of Formula (III) is preferably reduced with lithium tetrahydridoaluminate in a dry aprotic solvent such as diglyme, at elevated temperatures, as described by Rosi et al., "Stereoselective reduction of β- and ω-alkynols to the corresponding (E)-alkenols by lithium tetrahydridoaluminate," *Synthesis* 1977:561–562, which is hereby incorporated by reference. Preferably, the reduction is conducted at 120°–140° C. for 2–5 hours. Heating at higher temperatures or for longer times or both results in product contaminated with over-reduced and isomerizated polyenols and, consequently, is preferably avoided.

The dienynol of Formula (III) can be prepared by a variety of synthetic pathways. In a preferred synthetic scheme, a dienyl halide having the formula:

  [IV]

wherein X is a halogen atom, is alkylated with an alkali metal salt of a protected 3-butynol having the formula:

  [V]

wherein M is an alkali metal and Y is an alcohol protecting group, thus producing a protected dienynyl alcohol having the formula:

  [VI]

wherein Y is the same alcohol protecting group used to protect the butynol of Formula (V). X, the halogen atom in Formula (IV), can be chlorine, bromine or iodine, preferably bromine. The akali metal which forms the salt of the protected 3-butynol, M in Formula (V), can be sodium, potassium, or, preferably, lithium. The protected 3-butynol alkali metal salt can be prepared by treating the corresponding 3-butynol with an alkyl alkali metal compound, such as, for example, n-butyllithium, in cold, dry aprotic solvent, such as, for example, tetrahydrofuran, diglyme, glyme, ethyl ether, or an alkane solvent. The 3-butynol alkali metal salt can be reacted, without further purification, with the dienyl halide dissolved in a dry, aprotic solvent, preferably having Lewis base activity, such as, for example, hexamethylphosphorous triamide ("HMPT"), or, preferably, 1,3-dimethyl-3, 4,5,6-tetrahydro-2(1H)-pyrimidine. The reaction is carried out for a time period from 0.1 to 2.0 hours, preferably 0.5 hours, at a temperature of −10° to 5° C., preferably 0° C. The reaction is advantageously heated or cooled, depending on the reactivity of the alkali metal employed. Where the lithium salt of the 3-butynol is used, the especially exothermic reaction can be controlled with a cooling bath. The protected dienynol is then deprotected, thereby providing the dienynol of Formula (III). Y, the alcohol protecting group in Formula (V) and Formula (VI), can be any group which inhibits displacement of the hydroxyl in a nucleophilic attack. Preferably, Y is tetrahydropyranyl. Other suitable alcohol protecting groups are described in Kocienski, *Protecting Groups*, Stuttgart: Thieme Publishers, 1994, which is hereby incorporated by reference, such as, for example, benzyl, benzhydryl, trityl, and trimethyl silyl. The method of deprotection depends on the nature of the protecting agent. Where the protecting agent is benzyl, deprotection may be effected by acid treatment or by mild hydrogenation. Where the preferred tetrahydropyranyl protecting group is employed, deprotection can be effected with an acid in a polar solvent, preferably with inactivated ion exchanger, such as DOWEX™ (Dow Chemical, Midland, Mich.), in methanol.

Various synthetic schemes can be employed to provide a dienyl halide of Formula (IV) in the aforedescribed preferred preparation of the Formula (VI) dienynol. In a preferred method, a protected 4-pentyn-1-ol, having the formula:

[VII]

wherein Z is an alcohol protecting group, is converted into a Grignard reagent, and then reacted with pentynyl tosylate to form a diyne having the formula:

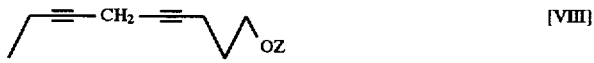
[VIII]

wherein Z is the same alcohol protecting group used to protect the pentynol of Formula (VII). The reaction is carried out in a dry, aprotic solvent, such as tetrahydrofuran, glyme, diglyme or ethyl ether, with tetrahydrofuran being preferred. The reaction is effected by slowly mixing the reactants, preferably by dropwise addition of the tosylate to the Grignard reagent, at a temperature of −5° to 10° C., preferably 0° C., followed by stirring the mixture for a period of 6 to 15 hours, preferably 12 hours, at 10° to 50° C., preferably 30° C. The Grignard reaction can be catalyzed, for example, by cuprous iodide, as described by Millar et al., "Short synthesis of 1,3Z,6Z,9Z-tetraene hydrocarbons. Lepidopteran sex attractants," *Can. J. Chem.* 64:2427–2430 (1986), which is hereby incorporated by reference, or, preferably, by a cuprous bromide-methyl sulfide complex. Suitable alcohol protecting groups include benzyl, benzhydryl, trityl, and tetrahydropyranyl and are reviewed in Kocienski, *Protecting Groups*, Stuttgart: Thieme Publishers (1994), which is hereby incorporated by reference. Preferably, Z is tetrahydropyranyl, and the protected 4-pentyn-1-ol is 1-(tetrahydropyran-2-yloxy)-4-pentyne. Where the preferred protecting group is employed, the diyne formed is 1-(tetrahydropyran-2-yloxy)-4,7-decadiene (Formula (VIII), Z=tetrahydropyranyl).

Alternatively, 1-(tetrahydropyran-2-yloxy)-4,7-decadiene, and analogs thereof, can be prepared using the coupling method described in Lapitskaya et al., "A chemoselective synthesis of functionalized 1,4-alkadiynes (skipped diacetylenes), *Synthesis*, 1993:65–66, which is hereby incorporated by reference. Because of its instability, the diyne is preferably used immediately and without further purification.

The diyne is then hydroborated, such as by reaction with an alkylborane, preferably a dicyclohexylborane, the preparation and use of which are detailed in Brown et al., "Hydroboration 45. New, convenient preparation of representative borane reagents utilizing borane-methyl sulphide," *J. Org. Chem.* 42:1392–72 (1977), which is hereby incorporated by reference. The reaction is carried out in an aprotic solvent, such as benzene, toluene, xylenes, or, preferably, tetrahydrofuran, for a period of 5 to 15 hours, preferably 12 hours, at a temperature of 10° to 50° C., preferably 30° C. The hydroboration product, a vinyl borane, is then hydrolyzed to the vinyl borate by stirring for 5 to 10 hours, preferably 7 hours, at −10° to 10° C., preferably 0° C., with a weak acid, preferably acetic acid. After basifying the reaction mixture, with, for example, sodium hydroxide, the vinyl borate is then carefully oxidized, preferably with hydrogen peroxide, at 10° to 50° C., preferably 30° C., for a time period of 0.05 to 2 hours, preferably 1 hour, to form a mixture of the protected and deprotected dienyl alcohol.

The mixture is then converted into dienyl halide by reaction of the mixture with a suitable halogenating reagent. Such suitable reagents include bromine and mixtures of tetrabromomethane and triphenyl phosphine, as described in Wagner et al., "Direct conversion of tetrahydropyranylated alcohols to the corresponding bromides," *Tetrahedron Lett.*, 30:557–558 (1989) and Sonnett, "Direct conversion of an alcohol tetrahydropyranyl ether to a bromide, chloride, methyl ether, nitrile, or trifluoroacetate, *Synthetic Communications*, 6:21–26 (1976), which are hereby incorporated by reference. Alternatively, and preferably, conversion to the halide is effected by treating the mixture of dienyl alcohol and protected dienyl alcohol with triphenyl phosphine dibromide such as described by Bestmann et al., "Pheromones:87. An efficient synthesis of (6E,11Z)-6,11-hexadecadienyl acetate and (6E,11Z)-6,11-hexadecadienal: Female sex pheromone of *Antheraea pernyi* and *A. polyphemus* (Lepidoptera: Saturniidae)," *Synthesis*, 1992:1239–1241, which is hereby incorporated by reference. Briefly, the triphenylphosphine dibromide is formed by treating triphenylphosphine with $Br_2$ in a suitable solvent at −10° to 10° C., preferably 0° C., for 0.1 to 0.5 hours, preferably 0.35 hours. Suitable solvents include dichloromethane, chloroform, tetrachloroethane, and, preferably, dichloromethane. The reaction of triphenyl phosphine dibromide with dienyl alcohol mixture is carried out at 10° to 50° C., preferably at room temperature, for 0.5 to 2 hours, preferably 1 hour.

The present invention further relates to compounds described by Formula (II); Formula (III); Formula (IV), wherein X is a halogen atom, preferably chlorine, bromine or iodine, most preferably, bromine; and Formula (VI), wherein Y is an alcohol protecting group, preferably a benzyl, benzhydryl, trityl, trimethylsilyl, or tetrahydropyranyl, most preferably tetrahydropyranyl. These compounds, when treated in accordance with the procedures described hereinabove, form substances which attract moths.

The present invention further relates to an attractant blend comprising two or more compounds. The compounds are selected from the group consisting of a 3,8-tetradecadienyl acetate, a 3,11-tetradecadienyl acetate, an 8,11-tetradecadienyl acetate, and a 3,8,11-tetradecatrienyl acetate. Preferably, the 3,8-tetradecadienyl acetate is (3E,8Z)-3,8-tetradecadienyl acetate, the 3,11-tetradecadienyl acetate is (3E,11Z)-tetradecadienyl acetate, and the 8,11-tetradecadienyl acetate is (8Z,11Z)-8,11-tetradecadienyl acetate. It is also preferred that at least one of the compounds in the attractant blend be a 3,8,11-tetradecatrienyl acetate, most preferably (3E,8Z,11Z)-3,8,11-tetradecatrienyl acetate.

The compounds of the present invention are useful as attractants for moths, especially the moth *Scrobipalpuloides absoluta*. They may be used for attracting moths for purposes of studying the moths, for controlling the region they habitate, for controlling their ability to reproduce, and for controlling their lifespan. In addition, the compounds can be used for monitoring moth populations.

The present invention also relates to a moth trap which comprises a moth restraining member and a moth attractant used in conjunction with the restraining member. The restraining member can physically restrain, chemically restrain, or entrap the attracted moths. The restraining member can be an adhesive material, such as, for example, glue or tanglefoot. The restraining member can also be a mechanical barrier, such as a door constructed to allow moths to enter the trap but not exit. The restraining member can also be an electrical device which shocks the moth which has been attracted to the attractant, thereby rendering the moth incapable of escaping the trap. The trap may further comprise an insecticide, whose action is enhanced by the inability of the moth to readily escape from the restraint. The amount of insecticide used can be lethal for an exposed insect or at least sublethal but sufficient to incapacitate the moth in regard to escape. The trap can further comprise one or more supports on which one or more of the attractant, adhesive and insecticide can be placed. The support can be formed from any material suitable for supporting one or more of the attractant, adhesive and insecticide, such as, for example, cotton, rubber, plastic, canvas, wood, or cardboard.

Additionally or alternatively, the moth trap of the present invention can further comprise a dispenser which sustainedly releases the moth attractant contained therein into the atmosphere, preferably at a constant rate over a length of time. One suitable dispenser is described in U.S. Pat. No. 4,834,745 to Ogawa et al., which is hereby incorporated by reference. It comprises a barrier wall made of a polymeric material which is swellable with the attractant. The moth attractant, contained in an a hollow space defined by the barrier wall, permeates through the barrier wall and is released from the outer surface thereof in the form of a vapor.

The serviceable life of the dispenser depends on the selection of the polymeric material forming the barrier wall to match the respective attractant and the dimensions of the dispenser. Specifically, the equilibrium swelling of the polymeric material with the moth attractant should preferably be in the range from about 2 to about 6% by weight at 20° C. When the equilibrium swelling is smaller than 2% by weight, the rate of attractant emission is undesirably low, while, conversely, an equilibrium swelling larger that 6% by weight would result in an undesirably large rate of attractant emission.

The equilibrium swelling of a polymeric material is a parameter determined by the kind of the polymeric material. Polymeric materials suitable for use in the invention include polyethylene, polypropylene, copolymers of ethylene and vinyl acetate, polyvinyl chloride, cellulose acetate, formalized polyvinyl alcohol and the like, of which polyethylene and copolymers of ethylene and vinyl acetate containing 20% by weight or less of vinyl acetate are particularly preferred.

The shape and size of the dispenser are not critical. Suitable dispenser shapes include, for example, cylindrical, such as a capillary tube, sealed at both ends, spherical, ellipsoidal, or platelike. Preferably, the ratio of the outer surface area of the dispenser to the amount of attractant contained therein is optimized using the guiding principles discussed in U.S. Pat. No. 4,834,745 to Ogawa et al., which is hereby incorporated by reference. For instance, when the outer surface area of the dispenser is great relative to the amount of attractant contained therein, the rate of attractant emission can be undesirably large with a large difference between the initial and latest stages of serviceable life of the dispenser so that the serviceable life would be unduly decreased. On the other hand, when the ratio is too small, the rate of attractant emission can be undesirably low, so that the preferred concentration of the attractant is not maintained in the atmosphere.

Attractants, used in conjunction with the aforementioned dispensers, are released over a sustained period of time, which enhances their susceptibility to oxidative and photochemical decomposition during the serviceable life of the dispenser. When the attractant is susceptible to photochemical decomposition, photochemical decomposition can be decreased by forming the barrier wall of a polymeric material admixed with an ultraviolet absorber, dye, or pigment or by admixing the attractant with an ultraviolet absorber or an antioxidant. Suitable antioxidants include 2,6-di-tert-butyl-p-cresol ("BHT").

Further details regarding the attractant dispensers and their use are disclosed in, for example, U.S. Pat. No. 4,834,745 to Ogawa et al. and U.S. Pat. No. 4,600,146 to Ohno, which are hereby incorporated by reference.

The traps can be of any suitable shape. Preferably, they are cylindrical shaped with conical screen funnel entrances at each end. The trap can be placed in trees or shrubs or suspended from or attached to poles mounted in the ground. Preferably, the trap is placed from about 1 to about 2 meters, more preferably about 1.2 meters, above the ground with one opening facing the prevailing wind. The amount of attractant per trap can range from about 10 picograms to about 10 milligrams, preferably from about 1 nanogram to 1 microgram.

Further details regarding the use and construction of moth traps are disclosed in U.S. Pat. No. 4,147,771 to Struble et al., U.S. Pat. No. 5,236,715 to McDonough et al., U.S. Pat. No. 3,991,125 to Labovitz et al., U.S. Pat. No. 3,803,303 to McKibben et al., and U.S. Pat. No. 3,980,771 to Meijer et al., which are hereby incorporated by reference.

The present invention further provides a moth control composition comprising an insecticide and a moth attractant. Because many insecticides repel moths, the combination of an attractant and insecticide can have enhanced effectiveness over use of an insecticide alone. The insecticide/attractant moth control composition can be in the form of, for example, sprays, such as emulsifiable concentrates or wettable powders, aerosols, dusts, baits, granular formulations, and laminated slow release formulations. The attractants, combined with the insecticide and used without a support, can be spread over the area of moth infestation, preferably as a mist or a dust in a suitable carrier, such as vegetable oils, refined mineral oils, rubbers, plastics, silica, diatomaceous earth, and cellulose powder. Alternatively, the attractant can be combined with an insecticide in an amount sufficient to fatally injure but not restrain the moth on a support without a restraint. Suitable supports include those suitable for use in moth traps, examples of which are listed above. Insecticide/attractant moth control compositions on supports are advantageous, because they eliminate the need to spread insecticides unnecessarily. Alternatively, the insecticide/attractant moth control composition can be used in traps (that is, in conjunction with a moth restraining member), as described above.

Further details regarding the combination of attractants and insecticides in moth control compositions in sprays, on supports or in traps are disclosed in, for example, U.S. Pat. No. 5,236,715 to McDonough et al., which is hereby incorporated by reference.

Suitable insecticides for use in the aforementioned moth traps and moth control compositions include, for example, organophosphates, such as diazinon, chlorpyrifos, propetamphos or acephate, carbamates, such as propoxur, pyrethroids, such as cypermethrin, sulfluramids, insect growth regulators, or mixtures thereof. S,S'-(2-dimethylaminotrimethylene) bis(thiocarbamate) ("Cartap"), ethyl 2-dimethoxythiophosphorylthio-2-phenylacetate ("Phenthoate"), available commercially under the name ELSAN™ (Rhodia Agro), 1-(2-chlorobenzoyl)-3-(4-trifluoromethoxyphenyl)urea ("Triflumuron"), available commercial under the name ALSYSTIN™ (Bayer), and abamectin, available commercially under the name VERMECTIN™ (Merck), are preferred. Further details respecting these and other suitable insecticides are disclosed in Worthing, ed., *The Pesticide Manual*, 9th Ed., British Crop Protection Council, which is hereby incorporated by reference.

The invention further relates to a moth control composition comprising a biocontrol agent and a moth attractant. For the purposes of the present invention, a biocontrol agent is defined as any biological enemy (e.g., predator, pathogen, parasite) of the moth. Examples of biocontrol agents include pathogenic nematodes, fungi, yeast, bacteria, and viruses. In use, the attractant lures moths to the biocontrol agent/attractant moth control composition where the moths are infected with the biocontrol agent. The moths then return to the general moth population and disseminate the agent to the rest of the population. As a result, an entire infestation of moths can be reduced by luring and infecting a few members of the population with the appropriate pathogen.

The biocontrol agent/attractant moth control composition can be in the form of, for example, a spray, such as emulsifiable concentrates or wettable powders, aerosols, dusts, baits, granular formulations, and laminated slow release formulations. The attractants can be combined with the biocontrol agent, without a support, and spread over the area of moth infestation, preferably as a mist or as a dust in a suitable carrier, such as vegetable oils, refined mineral oils, rubbers plastics, silica, diatomaceous earth, and cellulose powder. Alternatively, the attractant can be combined with the agent on a support. Suitable supports include those suitable for use in moth traps, examples of which are listed above. Biocontrol agent/attractant moth control compositions on supports are advantageous, because they eliminate the need to spread biocontrol agents unnecessarily. Because the mechanism by which biocontrol agents operate requires return of the infected moth to the population, the support is preferably used without an insecticide or moth restraining member.

It is also envisioned that chemosterilants can be used in conjunction with the moth attractants of the present invention to attract and sterilize male moths. Methods for exposing moths with the chemosterilant/attractant moth control compositions are analogous to those used for exposing moths with the biocontrol agent/attractant compositions.

Further details regarding the preparation and use of combination of biocontrol agent/attractant and chemosterilant/attractant moth control compositions are disclosed, for example, in U.S. Pat. No. 5,236,715 to McDonough et al., which is hereby incorporated by reference.

The moth attractants of the present invention can also be used to disrupt mating of moths within a particular area. This method includes providing in the particular area a quantity of an attractant above that emanating from moths, preferably a quantity sufficient to prevent pheromone communication. In this manner, potential mates are prevented from finding each other, thus disrupting the ability of the moths to mate. The moth attractant can be provided to the particular area by dispersing, such as by spraying or depositing, the attractant over or in the particular area. Suitable carriers, such as vegetable oils, refined mineral oils, rubbers, plastics, silica, diatomaceous earth, and cellulose powder, can be advantageously employed to aid in dispersing the attractant. Alternatively, the attractant can be provided by evaporating the attractant, its solution, or its emulsion from a number of places in the particular area. Further details regarding disruption of moth mating are disclosed in U.S. Pat. No. 3,980,771 to Meijer et al., which is hereby incorporated by reference.

The present invention also provides a method for attracting moths to a particular location comprising providing at the particular location about 10 picograms to about 10 milligrams, preferably about 1 nanogram to about 1 microgram of the moth attractants of the present invention. Proximate to the particular location, moths attracted with the aforementioned method can be exposed to an agent which impairs their ability to mate, thereby controlling the moth population. Suitable moth control agents include, for example, moth restraining devices, insecticides, biocontrol agents, or chemosterilants, as described above. The method of attracting moths can also be used to draw moths away from sensitive locations to less sensitive locations, such as, for example, from a region where tomatoes are cultivated to a region where no tomatoes are cultivated.

It is also envisioned that the moth attractants of the present invention can be used to detect the location and boundaries of localized moth infestation and to monitor moth populations. Such a method can employ the traps of the present invention, placed at strategic locations within and near the suspected area of infestation. The quantity of moths trapped at each of these strategic locations would permit a mapping of the boundaries of moth infestation. Alternatively, the attractant can be placed on a support and the number of moths approaching the support counted electronically, optically, mechanically, or otherwise, without trapping, restraining, killing, or otherwise incapacitating the moths. In this way, an estimate of the moth population density can be obtained. The area of localized infestation can then be treated with biocontrol agents or insecticides or both, thus permitting efficient and directed use of such biocontrol agents and insecticides. Further details regarding the use of moth attractants to detect and locate areas of moth infestation are disclosed in U.S. Pat. No. 5,236,715 to McDonough et al., and U.S. Pat. No. 3,980,771 to Meijer et al., which are hereby incorporated by reference.

In each of the aforementioned moth traps, moth control compositions, including those comprising insecticides, biocontrol agents and chemosterilants, and methods of using moth attractants, the moth attractant referred to therein can be a 3,8-tetradecadienyl acetate, a 3,11-tetradecadienyl acetate, an 8,11-tetradecadienyl acetate, a 3,8,11-tetradecatrienyl acetate, or mixtures thereof. It is preferred that the moth attractant be isolated. It is further preferred that the isolated moth attractant be substantially pure. Preferably, the 3,8-tetradecadienyl acetate is (3E,8Z)-3,8-tetradecadienyl acetate, the 3,11-tetradecadienyl acetate is (3E,11Z)-3,11-tetradecadienyl acetate, and the 8,11-tetradecadienyl acetate is (8Z,11Z)-8,11-tetradecadienyl acetate. Suitable 3,8,11-tetradecatrienyl acetates include (3E,8E,11E)-3,8,11-tetradecatrienyl acetate, (3E,8E,11Z)-3,8,11-tetradecatrienyl acetate, (3E,8Z,11E)-3,8,11-tetradecatrienyl acetate, (3E,8Z,11Z)-3,8,11-tetradecatrienyl acetate, (3Z,8E,11E)-3,8,11-tetradecatrienyl acetate, (3Z,8E,11Z)-3,8,11-tetradecatrienyl acetate, (3Z,8Z,11E)-3,8,11-tetradecatrienyl acetate, and (3Z,8Z,11Z)-3,8,11-tetradecatrienyl acetate. Preferably, the attractant includes a 3,8,11-tetradecatrienyl acetate and, more preferably, (3E,8Z,11Z)-3,8,11-tetradecatrienyl acetate. Alternatively, the attractant can be an attractant blend of the present invention.

In each of the aforementioned methods of using moth attractants, including the methods of attracting moths, controlling a population of moths, disrupting mating of moths, detecting the location and boundaries of localized moth infestation, and moth sterilization, the moths referred to therein are preferably *Scrobipalpuloides absoluta*.

The present invention is further illustrated by the following examples.

EXAMPLES

Example 1

Materials and Methods

*S. absoluta* larvae were collected from tomato plantations near the Federal University of Viçosa, and reared in the laboratory on a diet of fresh tomato leaves (*Licopersicum esculantum*). Pupae were collected every three days and sexed as described by Coelho et al., "Biologia, quetotaxia da larva e descricão da pupa da traça-do-tomateiro," *Pesqui. Agrop. Bras.*, 22:129–135 (1987), which is hereby incorporated by reference. Five specimens of each sex were placed in glass tubes (8.0×2.5 cm) and insects of each sex were kept in a different room. All the insects were maintained at a temperature of 23°±2° C., under a 14:10-hr light-dark cycle, and a relative humidity of 75±5%. After emergence, the females were observed during the scotophase and the beginning of the photophase to recognize their calling time and behavior.

Hydrazine hydrate and hydrogen peroxide (30 wt. % solution in water) were purchased from Mallinckrodt (Chesterfield, Mo.) and Fisher Chemical Co. (Fair Lawn, N.J.), respectively. Butyllithium (1.6M and 2.5M solutions in hexane), 2-(3-butynyloxy)tetrahydro-2H-pyran (1-(tetrahydopyran-2-yloxy)-3-butyne), lithium tetrahydridoaluminate, borane-methylsulfide complex, Cu(I)Br.Me$_2$S complex, and p-toluenesulfonyl chloride from Aldrich Chemical Co. (Milwaukee, Wis.), and bromine and triphenylphosphine from Fluka Chemical Co. (Ronkonkoma, N.Y.), were used as purchased. 1-(Tetrahydopyran-2-yloxy)-4-pentyne was prepared from the corresponding alcohol using the methods described in Robertson, "Adducts of tert-alcohols containing an ethynyl group with dihydropyran. Potentially useful intermediates," *J. Org. Chem.* 25:931–932 (1960), the disclosure of which is hereby incorporated by reference. Column chromatography was run on silica gel (Merck, H 60), and reactions were monitored by TLC on Baker-flex Silica gel IB2-F plates (J. T. Baker). Silver nitrate column chromatography was done on silica gel impregnated with AgNO$_3$ (20% of AgNO$_3$ on silica gel Merck H 60).

NMR spectra were recorded on an Unity-200 ($^1$H, 200 MHz, Varian), on a Unity-400 ($^1$H NMR, 400 MHz, $^{13}$C NMR, 100.6 MHz, Varian), and on a Unity-500 ($^1$H NMR, 500 MHz and $^{13}$C NMR, 125.7 MHz, Varian) as CDCl$_3$ solutions at room temperature. Chemical shifts, given in ppm, are expressed as δ values measured from the residual CHCl$_3$ signal (7.26 ppm). Vapor phase infrared spectra were recorded using a Hewlett-Packard (HP) 5965 A IRD coupled to a HP 5890 GC. Electron impact (70 eV) spectra were obtained using a HP 5890 GC coupled to an ITD ion trap detector (Finnigan). Fast atom bombardment (FAB, in a glycerin matrix) mass spectra were obtained on a ZAB-Q (VG) instrument. For GC analysis a Supelco fused-silica capillary column (30 m×0.25 mm) coated with SE-54 (0.25 µm) fitted in a HP 5890 GC equipped with a flame-ionization (FID) detector was used. Synthetic samples (about 1 mg/ml in hexane) were injected in split mode using a temperature program of 60° C. for 4 min, 10° C./min to 270° C., and held for 20 min. Analyses of natural samples were carried out using fused-silica capillary columns (0.22 mm×30 m) coated with free-fatty-acid phase ("FFAP") or DB-5 stationary phases (J&W Scientific, Folsom, Calif.).

Example 2

Preliminary studies

Preliminary studies on the mating behavior of *S. absoluta* showed that the females attract males even on the first day after emergence. Over 50% of females (n=34) in a laboratory colony showed maximum calling activity from 5:30 to 7:30 AM. Bioassays conducted with calling caged females in a wind-tunnel showed that the males respond and fly immediately to females during this short period of time during which the females release pheromones. During the calling period, the females extrude the ovipositor and expose the intersegmental glandular membrane. The intersegmental membrane ("pheromone gland") of calling females was excised and extracted with hexane.

A preliminary examination of hexane extracts made from excised pheromone-producing glands of females that were actively attracting conspecific males, using capillary gas chromatography-mass spectrometry, showed the presence of two significant GC peaks in the region where lepidopteran pheromones usually appear, as indicated in FIG. 1. The minor constituent was partially characterized by GC/MS as a tetradecadienyl acetate. The mass spectrum corresponding to the major peak (90%) is shown in FIG. 2. From the base peak at m/z 43, it was apparent that this component is an acetate, and the ion produced by loss of acetic acid, (M$^+$-60) at m/z 190, indicated that the compound is a tetradecatrienyl acetate. A comparison of the integrated GC peak area is this component with that of an external standard showed that the amount of this constituent obtainable from each female gland to be about 1–5 ng.

An attractive strategy to locate the position and configuration of the three double bonds is a partial reduction of the material to obtain a product mixture containing all possible monoene acetates, since excellent techniques are available for the determination of double bonds in monoenes. Partial reduction was effected by the diimide procedure described by Corey et al., "Chemistry of diimide. Some new systems for the hydrogenation of multiple bonds," *Tetrahedron Lett.* 1961:347–352 and Yamaoka et al., "Determination of geometric configuration in minute amounts of highly unsaturated termite trail pheromone by capillary gas chromatography in combination with mass spectrometry and fourier-transform infrared spectroscopy," *J. Chromatogr.*, 399:259–267 (1987), which are hereby incorporated by reference. The exact conditions required to carry out this two-step procedure using less than 100 ng of the starting material were worked out using (4Z,7Z,10Z)-4,7,10-tetradecatrienyl acetate as a model. Once the optimal conditions were established, the natural pheromone extract was subjected to a partial diimide reduction as follows. An ethanol extract containing 125 female sex glands was concentrated to a few microliters and mixed with a solution of hydrazine (10 μl, 10% in ethanol) and hydrogen peroxide (10 μl, 0.6% in ethanol). The mixture was heated at 60° C. for 2.5 hr and allowed to cool to room temperature. It was acidified with dilute HCl and extracted with hexane (3×15 μl). The combined hexane layers were reduced to 2–3 μl and reconstituted to 10 μl with hexane. One μl of this extract, together with hexadecane and tetracosane as internal standards, was analyzed by GC-MS.

GC-MS analysis of the reduced mixture showed the presence of three tetradecenyl acetates along with doubly unsaturated and saturated acetates. In order to identify these three tetradecenyl acetates precisely, the mass spectra as well as the GC retention times of all 23 possible tetradecenyl acetates on two different gas chromatographic stationary phases (DBWax, and DB-23) were measured, and these data were compared to those obtained for the three tetradecenyl acetates that resulted from partial reduction of the natural pheromone. In this way, two of the monoenes derived from the natural pheromone were identified unambiguously as (E)-3-tetradecenyl acetate and (Z)-8-tetradecenyl acetate. However, retention data alone could not establish the identity of the third isomer, since the retention times of (Z)-11-tetradecenyl acetate and 13-tetradecenyl acetate were very similar on both GC phases. To establish the identity of the third tetradecenyl acetate, the mixture was converted into a mixture of the corresponding dimethyl disulfide ("DMDS") adducts using the methods described in Francis et al., "Alkylthiolation for the determination of double bond position in linear alkenes," *J. Chromatogr.* 219:379–384 (1981), Buser et al., *Anal. Chem.*, 55:818–822 (1983), and Attygalle et al., *Angew. Chem. Int. Ed. Engl.*, 27:460–478 (1988), which are hereby incorporated by reference. GC-MS analysis of this mixture showed the expected presence of DMDS adduct of an 8-tetradecenyl acetate (m/z(%), 348 (M+,10), 217(40),131(23)), and that of an 11-tetradecenyl acetate (m/z (%),348(M+,15),259(95),89(38)). Retention times of these two adducts on a DB-1 capillary column were identical to those obtained from the DMDS derivatives of authentic (Z)-8-tetradecenyl acetate and (Z)-11-tetradecenyl acetate. Based on these results, the triply unsaturated compound was identified as (3E,8Z,11Z)-3,8,11-tetradecatrienyl acetate.

The structure and stereochemistry was further supported by synthesis of (3E,8Z,11Z)-3,8,11-tetradecatrienyl acetate, as described below in detail with reference to the following reaction sequence:

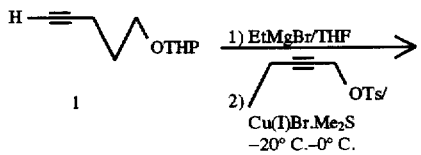

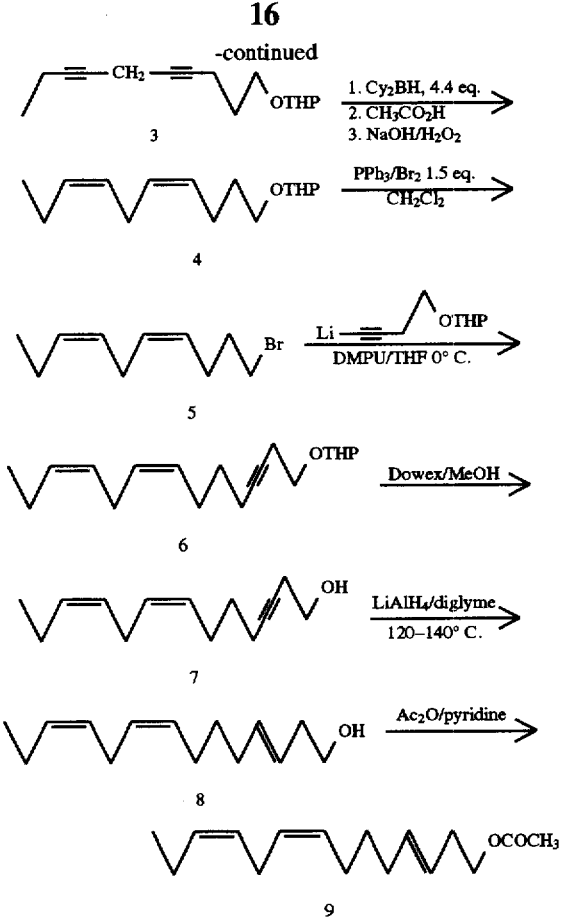

Example 3

Preparation of 2-pentyn-1-yl p-toluenesulfonate (2)

Propargyl alcohol (Aldrich Chemical Co., St. Louis, Mo.) (11.8 g, 200 mmol) was added dropwise (30 min) to a suspension of lithium amide in liquid ammonia (600 mL), formed from lithium wire (2.8 g, 0.4 mol), followed by ethyl bromide (21.8 g, 200 mmol) which was added during a period of 45 min. The reaction mixture was stirred for 1 hr in boiling ammonia. Usual work-up and distillation under reduced pressure afforded 2-pentyn-1-ol (14.2 g, 85% yield) of b.p. 63°–66° C./23 torr. $^1$H NMR (200 MHz) δ: 4.22 (bs, 2H, CH$_2$O-1), 2.21 (tq, J=2.2, 2.2, 2.2, 7.5, 7.5 Hz, 2H, CH$_2$-4), 1.80 (bs, 1H, OH), 1.12 (t, J=7.5, 7.5 Hz, 3H, CH$_3$-5).

A solution of 2-pentyn-1-ol (8.40 g, 100 mmol) in THF (60 mL) was treated with p-toluenesulfonyl chloride (23.9 g, 125 mmol) at −10° C., followed by pulverized KOH (11.3 g, 200 mmol) without allowing the temperature to exceed −5° C. After 1.5 hours of stirring at −10° C., 50 mL of saturated brine was added and the product extracted into CH$_2$Cl$_2$. The product, 2-pentyn-1-yl p-toluenesulphonate (2), was isolated by flash chromatography (18.17 g 76.4% yield). $^1$H NMR (200 MHz) δ: 7.81 (d, J=8.4 Hz, 2H, arom. CH), 7.33 (d, J=7.9 Hz, 2H, arom. CH), 4.68 (t, J=2.2, 2.2 Hz, 2H, CH$_2$O-1), 2.44 (s, 3H, arom. CH$_3$), 2.13 (tq, J=2.2, 2.2, 2.2, 7.5, 7.5 Hz, 2H, CH$_2$-4), 1.00 (t, J=7.5, 7.5 Hz, 3H, CH$_3$-5).

Example 4

Preparation of 1-(tetrahydropyran-2-yloxy)-4,7-decadiyne (3)

A solution of 1-(tetrahydropyran-2-yloxy)-4-pentyne (1) (8.40 g, 50 mmol) in dry THF (30 mL) was treated with C₂H₅MgBr in THF (30 mL) which was freshly prepared from ethyl bromide (5.99 g, 55 mmol) and magnesium (1.58 g, 66 mmol). After intensive evolution of ethane decreased, the mixture was refluxed at 60° C. for 1 hr. The solution was transferred into a suspension of Cu(I)Br.Me₂S complex (0.51 g, 5 mol %) in dry THF (50 mL). The solid dissolved gradually and formed dark solution which was stirred at room temperature for 20 min. The mixture was cooled on an ice bath and a solution of 2 (8.4 g, 35 mmol) in dry THF (10 mL) was added dropwise during 30 min. After an additional 1 hr on the ice bath, the mixture was stirred at room temperature for 12 hr. The reaction was quenched with a solution (50 mL) containing 1:2 (v/v) mixture of concentrated aqueous ammonia and saturated NH₄Cl solution. The usual work-up afforded a crude product (11.6 g), containing 98% of the desired product (3) and 2% of the tosylate. ¹H NMR (200 MHz) δ: 4.60 (m, 1H, CH-2'), 3.82 (m, 2H, CH₂-6' and 1), 3.45 (m, 2H, CH₂-6' and 1), 3.10 (dt, J=4×2.3 Hz, 2H, =CH—CH₂—CH=), 2.28 (m, 2H, CH₂-3), 2.16 (tq, J=7.6, 2.3, 2.4, 7.6, 7.6 Hz, 2H, CH₂-9), 1.8–1.4 (m, 8H, CH₂-2, -3', -4', and -5'), 1.11 (t, J=7.6, 7.6 Hz, 3H, CH₃-10). ¹³C NMR (100.6 MHz) δ: 98.7 (2'), 81.8 (7), 79.7 (5), 74.7 (8), 68.4 (4), 66.6 (1), 62.1 (6'), 30.7 (3'), 28.9 (2), 25.5 (4'), 19.5 (6), 15.7 (5'), 13.9 (3), 12.4 (9), 9.7 (10).

Example 5

Preparation of (4Z,7Z)-1-(tetrahydropyran-2-yloxy)-4,7-decadiene (4)

An ice-cooled solution of cyclohexene (24 ml, 240 mmol) in dry THF (50 ml) was treated with a borane-methyl sulfide complex solution in toluene (60 ml, 120 mmol) for 20 min. After an additional 20 min of stirring on an ice bath, the resulting suspension was stirred at room temperature for 2 hr. This dicyclohexylborane slurry was treated with a solution of 3, prepared in Example 4, (11.6 g, 49.8 mmol) in dry THF (50 mL) at 0° C. After 12 hr at room temperature, the mixture was treated with glacial acetic acid (40 mL) at 0° C., and stirred for 7 hr. The mixture was made basic with 5M NaOH, and carefully oxidized with H₂O₂ (30%, 40 ml) for 1 hr. The reaction products were extracted into ether, and cyclohexanol was distilled off using a Vigreux column under reduced pressure. Finally, 12.4 g of a crude oil was isolated which was shown by GC analysis to consist of a 1:1 mixture of 4 and (4Z,7Z)-4,7-decadien-1-ol. 4. ¹H NMR (200 MHz) δ: 5.38 (m, 4H, CH=CH -4, -5, -7, and -8), 4.57 (m, 1H, CH -2'), 3.72 (m, 2H, CH₂-6' and 1), 3.41 (m, 2H, CH₂-6' and 1), 2.77 (dd, J=5.6, 2.8 Hz, 2H, =CH—CH₂—CH=), 2.13 (m, 4H, CH₂-3, 9), 1.8–1.4 (m, 8H, CH₂-2, -3', -4', and -5'), 0.96 (t, J=7.5, 7.5 Hz, 3H, CH₃-10). MS [EI, m/z (%)] 169 (5), 153 (7), 135 (5), 123 (5), 109 (7), 95 (10), 85 (100), 67 (18). MS (FAB, m/z) 237 (M⁺-1).

4Z,7Z)-4,7-decadien-1-ol. ¹H NMR (200 MHz) δ5.37 (m, 4H, CH=CH -4, 5, 7, 8), 3.64 (m, 2H, CH₂-1), 2.77 (dd, J=5.1, 5.7 Hz, 2H, =CH—CH₂—=), 2.10 (m, 4H, CH₂-3, and -9), 1.64 (tt, J=6.5, 6.6, 7.0, 7.5 Hz, 2H, CH₂-2), 0.96 (t, J=7.5, 7.5 Hz, 3H, CH₃). ¹³C NMR (100.6 MHz) δ: 131.9 (8), 129.1 (5), 128.8 (7), 127.1 (4), 62.5 (1), 32.7 (2), 25.5 (6), 23.5 (3), 20.5 (9), 14.3 (10).

Example 6

Preparation of (4Z,7Z)-1-bromo-4,7-decadiene (5)

A solution of triphenylphosphine (20.9 g, 80 mmol) in CH₂Cl₂ (100 ml) was treated with Br₂ (7.8 g, 49 mmol) in CH₂Cl₂ (15 mL, 0° C.) and the mixture was stirred at room temperature for 20 min. Into the slightly yellow suspension that formed, the crude mixture of 4 and 4Z,7Z)-4,7-decadien-1-ol (12.4 g) in CH₂Cl₂ (15 ml) was added dropwise. After stirring for 1 hour, a solution of saturated NaHCO₃ (50 mL) and water (50 ml) were added. The mixture was extracted with pentane and combined extracts were stored overnight in a freezer. In this way, triphenylphosphine oxide could be crystallized and removed by filtration. Column chromatography followed by distillation at reduced pressure afforded 5 (3.48 g, 32% yield based on 1 of b.p. =80°–85° C./2.5 torr. ¹H NMR (200 MHz) δ: 5.37 (m, 4H, CH=CH), 3.41 (t, J=6.6, 6.6 Hz, 2H, CH₂—Br), 2.80 (dd, J=6.4, 6.5 Hz, 2H, =CH—CH₂—CH=), 2.21 (dt, J=7.0, 6.9, 6.8, 6.9 Hz, 2H, CH₂-3), 2.07 (dq, J=7.4 Hz, CH₂-9), 1.91 (tt, J=6.7, 6.6, 7.0, 7.0, 2H, CH₂-2), 0.97 (t, J=7.5, 7.5 Hz, 3H, CH₃). ¹³C NMR (100.6 MHz) δ: 132.1 (8), 129.8 (5), 127.6 (7), 127.0 (4), 33.4 (1), 32.5 (2), 25.6 (3), 25.5 (6), 20.6 (9), 14.3 (10). MS [EI, m/z (%)] 218 (M⁺, 15), 216 (17), 137 (6), 109 (13), 107 (18), 96 (14), 95 (78), 82 (18), 81 (74), 79 (22), 68 (27), 67 (100), 55 (17), 53 (15), 42 (11), 41 (38), 40 (40).

Example 7

Preparation of (8Z,11Z)-1-(tetrahydropyran-2-yloxy)-8,11-tetradecadien-3-yne (6)

A solution of 1-(tetrahydropyran-2-yloxy)-3-butyne (2.25 g, 14 mmol) in dry THF (15 ml) was treated at −50° C. with n-butyllithium hexane solution (11 ml, 17.5 mmol). After 15 min at −30° C., the mixture was kept at room temperature for 30 min. The mixture was then treated at 0° C. with 5 (3.0 g, 13.8 mmol) dissolved in 1,3-dimethyl-3,4,5,6-tetrahydro-2 (1H)-pyrimidine (DMPU) (15 mL) during 30 min. The reaction mixture was stirred 12 hr. at room temperature and quenched with saturated NH₄Cl solution (30 ml). The product (6) was removed with ether (3×50 ml) and purified by silica-gel flash chromatography (2.2 g, 55% yield). ¹H NMR (200 MHz) δ5.36 (m, 4H, CH=CH), 4.64 (m, 1H, CH-2'), 3.81 (m, 2H, CH₂-6' and 1), 3.54 (m, 2H, CH₂-6' and 1), 2.78 (dd, J=6.0, 6.0 Hz, 2H, =CH—CH₂—CH=), 2.47 (m, 4H, CH₂-2, and -5), 2.15 (m, 4H, CH₂-7, and -13), 1.8–1.4 (m, 8H, CH₂-6, -3', -4', and -5'), 0.96 (t, J=7.5, 7.6 Hz, 3H, CH₃). ¹³C NMR (100.6 MHz) δ: 131.8 (12), 128.9 (9, 11), 127.2 (8), 98.7 (2'), 81.0 (3), 76.6 (4), 66.2 (1), 62.2 (6'), 33.4 (2), 30.6 (3'), 28.9 (7), 26.2 (6), 25.5 (14), 25.4 (4'), 20.5 (5), 20.2 (13), 18.3 (5'), 14.3 (10). MS [EI, m/z (%)] 159 (7), 131 (9), 119 (8), 117 (9), 105 (8), 93 (11), 91 (16), 86 (12), 85 (100), 79 (18), 77 (11), 67 (36), 57 (16), 55 (15), 43 (29), 42 (16), 41 (51), 40 (24).

Example 8

Preparation of (8Z,11Z)-8,11-tetradecadien-3-yn-1-ol (7)

A solution of 6 (2.2 g, 7.5 mmol) in methanol (50 mL) was stirred with DOWEX™ 50W-X8 (Dow Chemical, Midland, Mich.) ion exchange resin (2 g) and the formation of 7 was monitored by TLC. The resin was removed by filtration and washed with methanol (3×20 mL). The alcohol 7 was purified by flash chromatography (1.3 g, 83% yield). ¹³H NMR (200 MHz) δ: 5.36 (m, 4H, CH=CH), 3.66 (t, J=6.1, 6.4 Hz, 2H, CH₂-1), 2.78 (t, J=6.4, 6.7 Hz, 2H, =CH—CH₂—CH=), 2.42 (tt, J=2.1, 2.4, 6.1, 6.4 Hz, 2H, CH₂-2), 2.16 (tt, J-2.1, 2.4, 7.0, 7.3 Hz, 2H, CH₂-5), 2.15 (m, 2H, CH₂-7), 2.06 (dq, J=7.3, 7.0, 7.3, 7.6 Hz, 2H, CH₂-13), 1.55 (tt, J=7.1, 7.3, 7.3, 7.3 Hz, 2H, CH₂-6), 0.96 (t, J=7.3, 7.6 Hz, 3H, CH₃-14). ¹³C NMR (100.6 MHz) δ: 131.9(12), 129.0(11), 128.8(9), 127.2(8), 82.3(3), 76.6(4), 61.3(1), 28.8 (7), 26.2(6), 25.5(10), 23.1(5), 20.5(2), 18.2(13), 14.2(14). MS [EI, m/z(%)] 161(15), 159(20), 145(30), 133(25), 131 (27), 119(34), 117(42), 105(42), 95(17), 93(27), 91(83), 79(76), 77(37), 69(22), 67(78), 65(29), 55(46), 53(39), 44(29), 43(24), 42(34), 41(100), 40(61).

Example 9

Preparation of (3E,8Z,11Z)-3,8,11-tetradecatrien-1-yl acetate (9)

A solution of 7 (0.4 g, 1.94 mmol) in dry diglyme (6 ml) was added slowly to a suspension of LiAlH$_4$ (0.228 g, 5.7 mmol) in dry diglyme (4 mL) at room temperature. The mixture was refluxed at 120°–140° C. for 5 hr and then cooled in an ice bath. Ethyl acetate (5 ml) was carefully added, and the mixture was poured into an ice and conc. HCl mixture (10 ml). Extraction with ether followed by flash chromatography afforded the alcohol (8) (0.225 g), which was acetylated with acetic anhydride (1 mL) and pyridine (3 mL) for 1 hr. Flash chromatography, and purification on 20% AgNO$_3$-impregnated silica gel afforded the desired product (3E,8Z,11Z)-3,8,11-tetradecatrien-1-yl acetate (9) (0.238 g), 50% yield based on (8Z, 11Z)-8,11-tetradecadien-3-yn-1-ol (7). $^1$H NMR (400 MHz) δ: 5:50 (dtt, J=15.2, 6.4, 6.4, 2.3, 2.4, Hz, 1H, trans=CH-3), 5.36 (m, 5H, CH=CH), 4.06 (t, J=6.7, 7.0 Hz, 2H, CH$_2$-1), 2.77 (dd, J=5.2, 6.8 Hz, 2H, =CH—CH$_2$—CH=), 2.31 (dt, J=2.3, 6.8, 7.0 Hz, 2H, CH$_2$-2), 2.06 (m, 6H, CH$_2$-5, -7, and -13), 2.04 (s, 3H, COCH$_3$), 1.42 (tt, J=7.3, 7.3, 7.6, 7.6 Hz,2H, CH$_2$-6), 0.97 (t, J=7.3, 7.3 Hz, 3H, CH$_3$). $^{13}$C NMR (100.6 MHz) δ: 171.1 (1'), 133.2(4), 131.8(12), 129.7(9), 128.3(11), 127.3(8), 125.4(3), 64.1(1), 32.1(2), 31.9(6), 29.3(7), 26.6(5), 25.6 (10), 21.0(2'), 20.5(13), 14.3(14). MS(EI, m/z(%)] 190(M$^+$ -60, 4), 161(9), 133(13), 119(9), 108(24), 107(15), 105(10), 93(54), 91(22), 80(43), 79(91), 67(68), 55(29), 43(100), 41(45). IR (gas phase, cm$^{-1}$) 3017 (cis=C—H str), 2936 (CH$_2$) 1761 (C=O), 1231, 1037 (C—O—), 967 (trans= C—H wag).

Example 10

Wind Tunnel Experiments

Synthetic samples of acetate 9 were applied as pentane solutions to rubber septa (cleaned by washing with dichloromethane for 20 hr in a soxhlet apparatus) which were used as baits in the wind tunnel. The attractivity of each bait, loaded with 10, 100, 1000, and 10,000 ng of acetate 9, was compared to that of 9 calling virgin females (1- to 4-day-old) in a cage. The control baits were treated with 100 μl of hexane. The wind tunnel (3.8 m×0.50 m) was operated at a flux speed of 30 cm/sec. The landing platform was 1 m away from the "take-off" platform. For each experiment, 3 males (1- to 3-day-old; Hickel et al., "Comportamento de chamamento e aspectos do comportamento de acasalamento de Scrobipalpula absoluta (Lepidoptera: Gelechiidae), sob condicões de campo, An. Soc. Entomol. Brasil. 20:173–182 (1991), the disclosure of which is hereby incorporated by reference) were placed on the "take-off" platform, and their behavioral responses were observed for 5 min and categorized as follows: 1=no response, 2=wing fanning, 3=none-oriented flight, 4=oriented flight, and 5=landing on the source. The test was repeated 10 times for each concentration.

The results are presented in FIG. 3. The males placed on the "take-off" platform showed significant behavioral responses at all concentrations of the pheromone that was tested. For example, males showed induced wing fanning, oriented flight, and landing on the source of the synthetic pheromone, even at the 10 ng level, the lowest amount tested. Naturally, the control dispensers loaded only with hexane did not induce any significant behavioral responses. Highest responses were observed at the 1000 ng level. At this concentration, 100% of the test insects (N=30) showed wing fanning, and 87% initiated an oriented flight toward the dispenser with 83% landing on the dispenser. The corresponding responses obtained by using nine calling females as the pheromone source were 38, 66, and 61%, respectively. The results in FIG. 3 indicate that a dispenser loaded with 1000 ng of the synthetic pheromone 9 is thoroughly competitive with the attractivity of a group of nine calling females.

Example 11

Field Tests

These experiments were carried out at a 20-ha tomato (Sata Clara variety) plantation in Araguari (State of Minas Gerais, Brazil) from Apr. 1, 1994, to Apr. 11, 1994. The traps were placed at a height of 1.20 m, and at 30-m intervals as suggested by Uchôa-Fernandes et al., In Congresso Brasileiro de Entomologia, Recife/PE, 13:639 1991) and Uchôa-Fernandes et al., "Field trapping of the tomato worm, Scrobipalpuloiodes absoluta (Meyrick) (Lepidoptera: Gelechiidae) using virgin females," Ann. Soc. Entomol. Brasil., 23:271–276 (1944), which are hereby incorporated by reference.

The first series of field experiments used five different trap designs, depicted in FIGS. 4A–4E. Trap A was made from white cylindrical PVC tubing (20 cm diameter×25 cm). Trap B was similar to Trap A; however, the cylinder was split into two halves and the two parts were connected with four metal wires to form two parallel 5-×-25 cm openings on both sides. Trap C was a delta type with a maximum vertical gap of 7-cm at the triangular opening, and a base area of 29×30 cm. The bottoms of traps A, B, and C were lined with removable sticky paper to catch insects. Trap D was made from a plastic tray (24×37×6 cm), to which an inverted V-shaped hood was attached with four metal rods. This house-shape trap was open from all four sides with a 8-cm opening at the minimum and 15-cm gap at the maximum opening in the middle. Trap E was made from two 20- and 32-cm diameter black plastic plates with 2-cm vertical sides, joined at three points with strong metal wire to form a cage. Moth traps D and E contained water in the bottom plate with a few drops of a neutral detergent to catch insects. Rubber septa loaded with 1 μg of acetate 9 were hung inside all traps as baits, and the number of insects caught in each trap (N=15) was counted each day.

Figure 5:
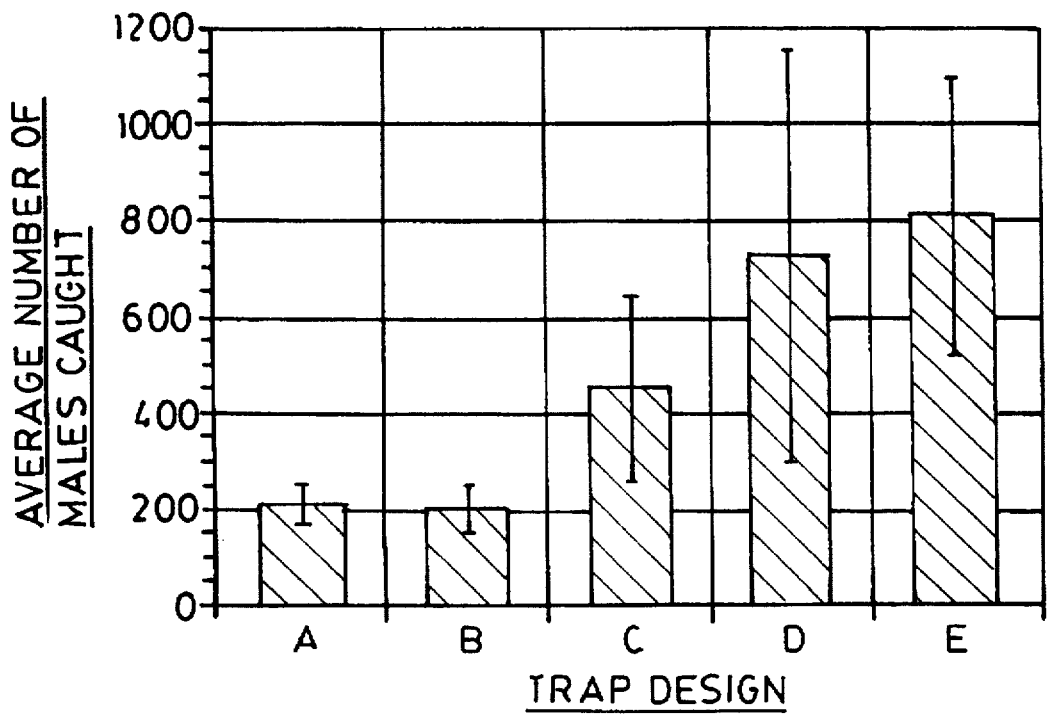

The results are presented in FIG. 5. While all traps caught a large number of S. absoluta males, designs D and E, which were open from all directions and used water containing a little detergent as the restraining agent, were much more efficient than traps A, B, and C. The most efficient design was trap E; a total number of 12,166 males was caught in one night in fifteen of these traps baited with dispensers loaded with 1 μg each of acetate 9.

In the second series of experiments (20 replications), rubber baits loaded with 1, 10, and 100 μg of acetate 9, or 100 μl of hexane, were used in E type traps. For comparison, a one-day-old virgin female in a cylindrical cage (4×4 cm) with the open ends covered by nylon mesh, was hung inside an E type trap. The number of males caught per trap was counted each morning.

Figure 6:
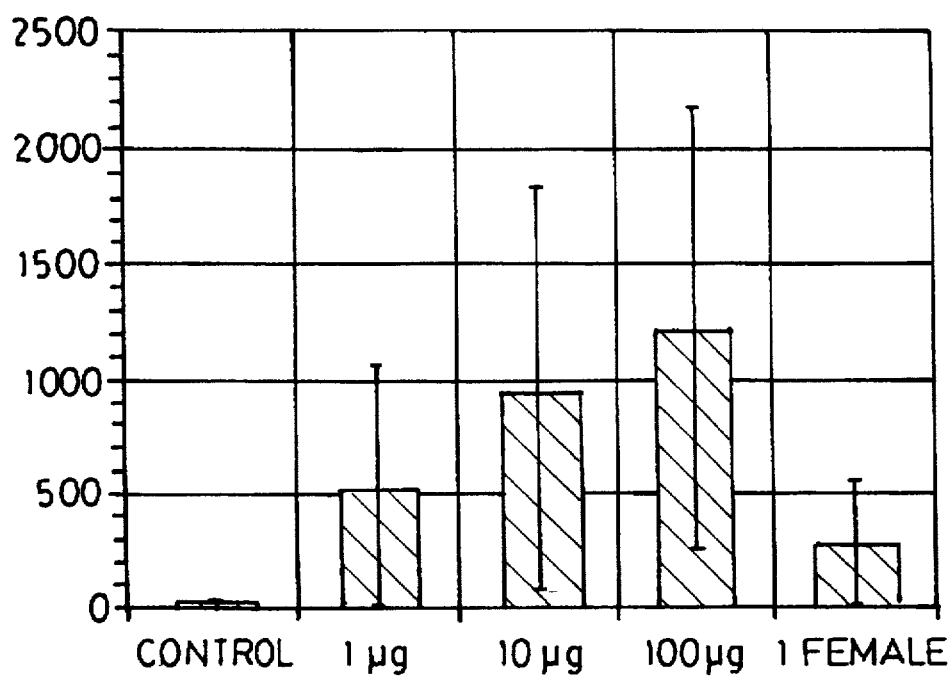

As the results presented in FIG. 6 show, all baited traps attracted very large numbers of S. absoluta males, proving further that (3Z,8Z,11Z)-3,8,11-tetradecatrienyl acetate (9) is a potent attractant. The number of males caught per trap gradually increased as the amount of pheromone loaded on the dispensers increased. The traps baited with 100 μg of 9 caught, on average, 1200 males per trap per night, while those baited with one one-day-old virgin female caught only 201 males. Even the traps baited with 1 μg of 9, which caught about 535 males per trap per night, were observed to compete well with virgin females in terms of attracting males in the field. Control traps having dispensers loaded only with hexane caught on average about 20 males per trap per night.

In the third series of experiments, two C type delta traps with sticky bottoms (27×20 cm) were baited with 1 μg of acetate 9. For a period of 24 hr, the number of males caught per trap at the end of each one hour period was counted, and the sticky cards were replaced when necessary.

Figure 7:
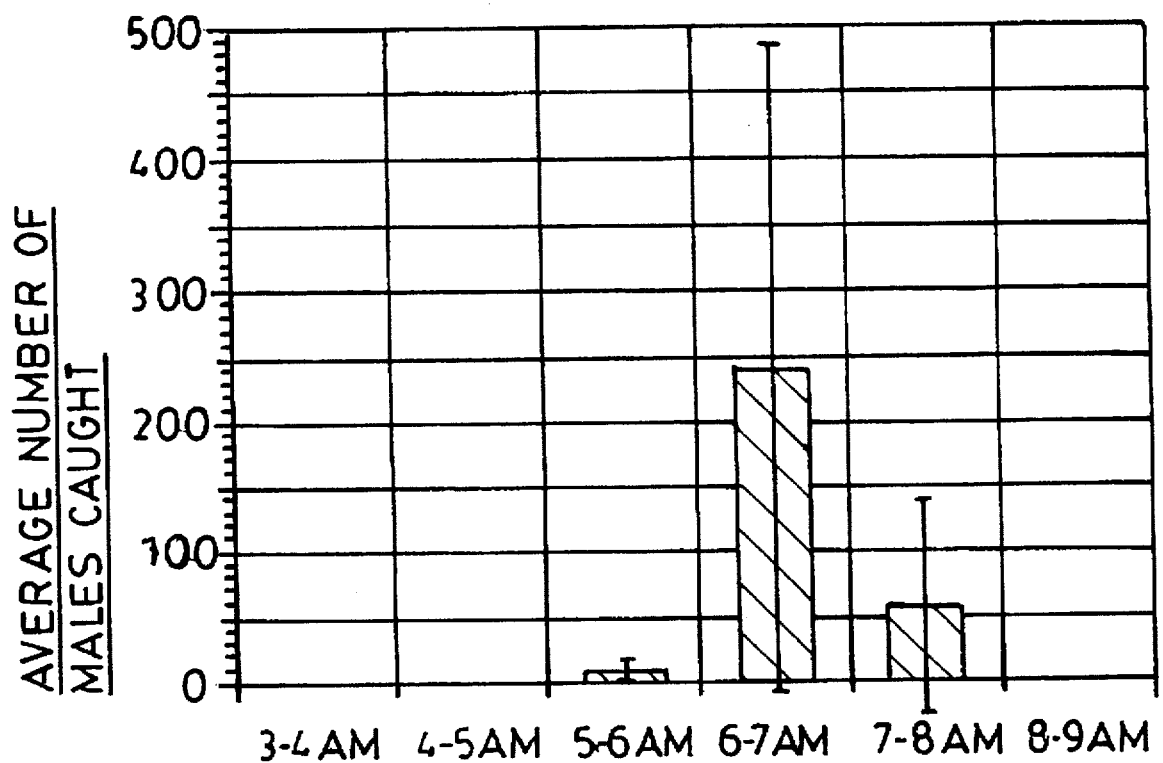

From the results of the third series of field tests, presented in FIG. 7, it is evident that the males of this species have a very distinct time period in which they actively search calling females. Appropriately baited traps caught an average of 240 males/trap during the period of 6:00 to 7:00 AM. Many fewer males were caught from 7.00 to 8.00 AM. However, the numbers caught became negligible after 8.00 AM. Since no males were caught before 5 AM or after 10 AM, data for the remainder of the 24-hr. time period are not included in FIG. 7.

Example 12

Preparation of (8Z,11Z)-8,11-tetradecadienyl acetate (14)

(8Z,11Z)-8,11-tetradecadienyl acetate was synthesized as described in detail below with reference to the following reaction sequence:

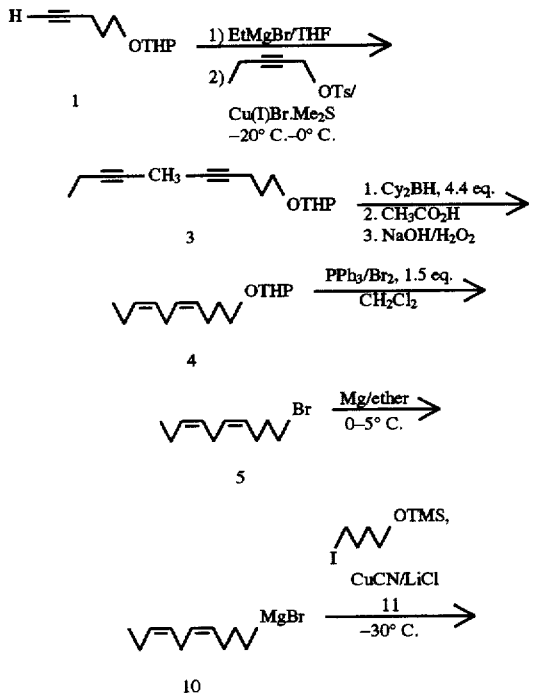

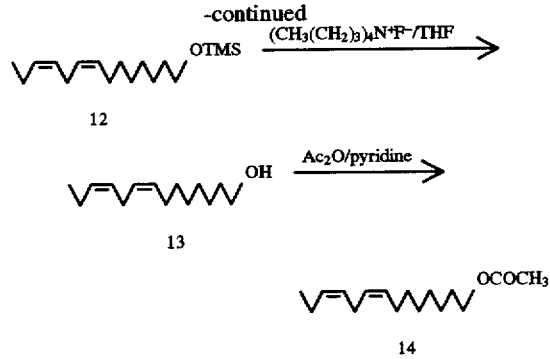

Magnesium turnings (30 mg, 1.28 mmol) were warmed (with a heating gun) and stirred for 1 hr under argon. The turnings were covered with dry THF (100 μl), and ten drops of a solution of 4Z,7Z)-1-bromo-4,7-decadiene (5) (200 mg, 0.925 mmol), prepared according to Example 6, in dry THF (3 ml) were added. The mixture was brought to reflux, and after the reaction started, the remaining solution of 5 was added dropwise at 0° C. over a period of 1.5 hr. The mixture was then stirred for 2 hr at room temperature to form the Grignard reagent (10).

Dry THF (3 ml) was treated with trimethylsilyl iodide (260 mg, 185 μl, 1.30 mmol) at room temperature and stirred for 15 min to form 4-trimethylsiloxybutyl iodide (11). A solution of CuCN. (LiCl)$_2$ in THF (1M, 100 μl) was added, and the mixture was cooled to –40° C. The above prepared solution of Grignard reagent 10, was then added over a period of 30 min, and a white precipitate formed. The mixture was stirred at –40° to –20° C. for 1 hr followed by an additional 1 hr at room temperature. The reaction was quenched with ammonium chloride solution and ammonia mixture (2:1, v/v), and the product was extracted with hexane/ether (1:1) mixture ($R_f$=0.60, 19:1 hexane/ethyl acetate, v/v). The crude (8Z,11Z)-trimethylsiloxy-8,11-tetradecadiene (12) was dissolved in THF (6 ml) and deprotected with tetrabutylammonium fluoride solution in THF (1M, 2 ml) to form the alcohol 13. Acetylation of the alcohol 13 with acetic anhydride/pyridine mixture (0.1 ml/1 ml) and purification by flash chromatography afforded (8Z,11Z)-8,11-tetradecadien-1-yl acetate (14) (80 mg) in 34% yield based on the starting bromide (5). $^1$H NMR (400 MHz) δ: 5.36 (m, 4H, CH=CH-8, 9, 11, 12), 4.05 (t, J=6.7, 7.0 Hz, 2H, CH$_2$-1), 2.77 (dd, J=6.4, 6.4 Hz, 2H, =CH—CH$_2$—CH=), 2.06 (m, 4H, CH$_2$-7, 13), 2.04 (s, 3H, —COCH$_3$), 1.60 (tt, J=7.3, 7.3, 7.6, 7.6 Hz, 2H, CH$_2$-6), 1.4–1.2 (m, 8H, CH$_2$-2, 3, 4, 5), 0.97 (t, J=7.3, 7.6 Hz, 3H, CH$_3$-14). $^{13}$C NMR (100.6 MHz) δ: 171.2 (C=O), 131.7 (=CH-12), 130.0 (=CH-11), 128.0 (=CH-9), 127.3 (=CH-8), 64.6 (CH$_2$-1), 29.5 (CH$_2$-2), 29.1 (CH$_2$-3, 4), 28.6 (CH$_2$-5), 27.2 (CH$_2$-6), 25.9 (CH$_2$-7), 25.5 (CH$_2$-10), 21.0 (CH$_3$C=O), 20.5 (CH$_2$-13), 14.3 (CH$_3$). MS [EI, m/z(%)] 252 (M$^+$,2), 209 (M$^+$-43, 1), 192 (M$^+$-60, 23), 163 (4); 149 (8), 135 (14), 121 (38), 110 (19), 107 (19), 95 (39), 93 (40), 82 (26), 81 (57), 79 (66), 67 (100), 55 (38), 43 (93), 41 (50). IR (gas phase, cm$^{-1}$) 3017 (cis=C—H str), 2936 (CH$_2$), 1761 (C=O), 1233, 1040 (—O—). (3E,8Z)-3,8-tetradecadienyl acetate was synthesized as described in detail below with reference to the following reaction sequence.

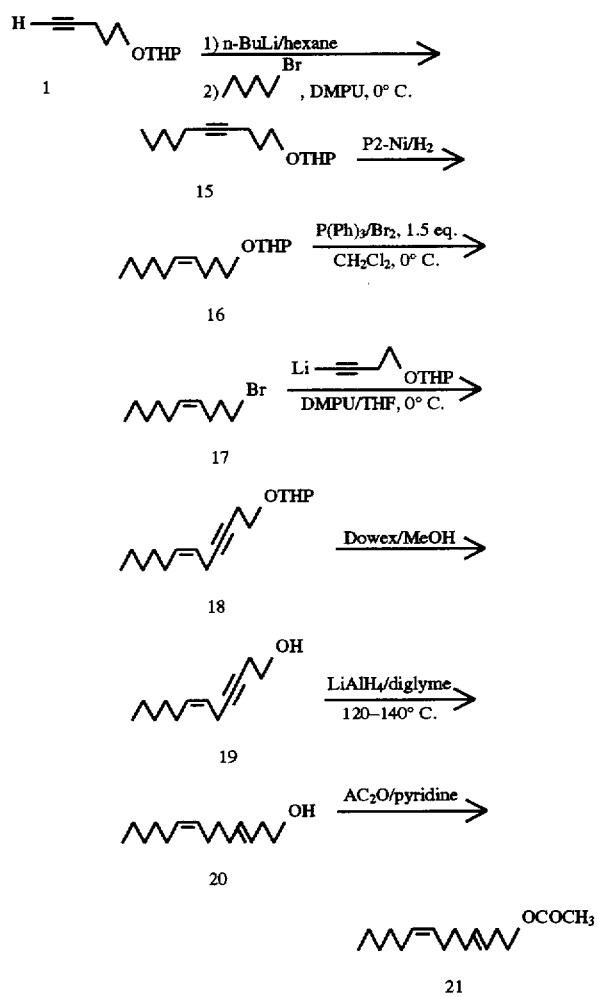

Example 13

Preparation of 1-(tetrahydropyran-2-yloxy)-4 decyne (15).

1-(Tetrahydopyran-2-yloxy)-4-pentyne (1) (0.66 g, 3.90 mmol) was metallated with n-butyllithium solution (2.5M) in hexane (1.87 ml, 1.2 eq.). Addition of a solution of n-pentyl bromide (0.725 ml, 1.5 eq.) in DMPU (2 ml) produced 0.54 g (58% yield) of the title compound (15). $^1$H NMR (200 MHz) δ: 4.60 (m, 1H, CH-2'), 3.65 (m, 4H, CH$_2$-1, 6'), 2.26 (tt, J=7.0, 7.0, 2.0, 2.0 Hz, 2H, CH$_2$-3), 2.13 (tt, J=7.0, 7.0, 2.5, 2.5 Hz, 2H, CH$_2$-6), 1.77 (tt, J=6.8, 6.8, 7.07 7.0 Hz, 2H, CH$_2$-2), 1.33 (m, 6H, CH$_2$-7, 8, 9), 1.52 (m, 6H, CH$_2$-3', 4', 5'), 0.89 (t, J=7.0 Hz, 3H, CH$_3$). MS [FAB, m/z(%)] 237 (M$^+$-1), 85 (100). IR (CCl$_4$, cm$^{-1}$) 2229, 1322, 1331, 1201, 1138, 1121, 1034.

Example 14

Preparation of 1-(tetrahydropyran-2-yloxy)-4-decen (16).

1-(Tetrahydropyran-2-yloxy)-4-decyne (15) (0.5 g, 2.1 mmol), prepared according to Example 13, was hydrogenated in ethanol (20 ml) over P2-Ni, formed from nickel acetate (75 mg) deactivated with ethylenediamine (0.2 ml) for 4 hr. After chromatography on silica gel, the product (16) (0.43 g) was obtained in 85% yield. GC (Rt): starting material 15, 22.18 min, 0.4%; desired product 16 21.59 min, 97.9%; the 4E isomer of 16, 21.75 min, 1.7%. $^1$H NMR (200 MHz) δ: 5.37 (m, 2H, CH=CH-4, 5), 4.58 (m, 1H, CH-2'), 3.60 (m, 4H, CH$_2$-1, 6'); 2.12 (M, 2H, CH$_2$-6); 2.04 (m, 2H, CH$_2$-3); 1.16 (tt, 2H, J=6.8, 6.8, 7.0, 7.0 Hz, CH$_2$-2), 1.4–1.9 (m, 6H, CH$_2$-3', 4', 5'), 1.29 (m, 6H, CH$_2$-7, 8, 9); 0.88 (t, 3H, J=7.0 Hz, CH$_3$). IR (CCl$_4$, cm$^{-1}$) 3007, 1653, 1201, 1138, 1120 1034. MS [FAB, m/z(%)] 239 (M$^+$-1), 85 (100).

Example 15

Preparation of Z-1-Bromodec-4-ene (17)

To an ice-cool solution of triphenylphosphine (0.72 g, 2.74 mmol) and bromine (0.41 g, 2.6 mmol) in CH$_2$Cl$_2$, a solution of (4Z)-1-(tetrahydropyran-2-yloxy)-4-decene (16) (0.41 g, 1.71 mmol), prepared according to Example 16, in methylene chloride was added dropwise. Isolation and purification by conventional means afforded the product 17 in 90% yield (0.33 g). $^1$H NMR (200 MHz) δ: 5.42 (dtt, J=11.0, 7.0, 7.0, 1.0, 1.0 Hz, 2H, CH=CH-4, 5); 3.41 (t, J=6.6, 6.6 Hz, 2H CH$_2$-1, 2.20 (dt, J=7.0, 7.0 Hz, 2H, CH$_2$-3); 2.04 (dr, J=6.5, 6.5 Hz, 2H, CH$_2$-6); 1.91 (tt, J=6.5, 6.5, 6.5 Hz, 2H, CH$_2$-2); 1.30 (m, 6H, CH$_2$-7, 8, 9); 0.89 (t, J=7.0 Hz, CH$_3$). MS [EI, m/z(%)] 220 (M$^+$-8), 218 (M$^+$, 8), 164 (12), 162 (12), 150 (23), 148 (23), 135 (8), 109 (12), 97 (44), 95 (14), 83 (55), 82 (14), 81 (37), 79 (15), 70 (21), 69 (100), 67 (39), 56 (29), 55 (93), 54 (20), 43 (21), 42 (20), 41 (92), 39 (30). IR (CCl$_4$, cm$^{-1}$) 3008 (cis CH=CH), 1246 (RCH$_2$CH$_2$Br), 649, 566 (C—Br).

Example 16

Preparation of (8Z)-1-(tetrahydropyran-2-yloxy)-8-tetradecen-3-yne (18)

1-(tetrahydropyran-2-yloxy)-3-butyne (0.30 g, 1.94 mmol) was metallated at 0° C. with n-butyllithium (2.0M) hexane solution (1.0 ml, 1.0 eq.). The lithium acetylide that formed was alkylated with the bromide 17 (0.20 g, 0.92 mmol), prepared according to Example 15, using 1,3-dimethyl-3,4,5,6-tetrahydro-2(1H)-pyrimidine ("DMPU") as the base. This reaction afforded 214 mg of the desired product 18. However, the product was contaminated with 0.05 g (29%) of nonpolar impurities, identified as (8Z)-1,8-tetradecadien-4-yne and 1-tetrahydropyran-2-yloxy)-3-butyne (28%), one of the starting materials. These impurities were removed from compound 18 by repeated column chromatography. $^1$H NMR (200 MHz) [18]δ: 5.35 (dtt, J=11.0, 7.0, 7.0, 1.0, 1.0 Hz, 2H, CH=CH-8, 9), 4.64 (m, 1H, CH-2'), 3.58 (m, 4H, CH$_2$-1, 6'), 2.46 (tt, J=7.5, 7.5, 2.5, 2.5 Hz, 2H, CH$_2$-2), 2.14 (tt, J=7.0, 7.0, 2.5, 2.5 Hz, 2H, CH$_2$-5), 2.10 (m, 2H, CH$_2$-7), 2.04 (dt, J=6.5, 6.5, 7.0 Hz, CH$_2$-10), 1.29 (m, 6H, CH$_2$-11, 12, 13), 1.9–1.4 (m, 8H, CH$_2$-6, 3', 4', 5'), 0.89 (t, J=7.0 Hz, 3H, CH$_3$). MS [EI, m/z(%)] [18] 133 (12), 107 (10), 85 (100), 67 (15), 55 (8). MS [FAB, m/z] 293.2 (M$^+$). IR (CCl$_4$, cm$^{-1}$) [18] 3007 (cis-CH=CH), 2232 (acetylenic), 1403, 1201, 1184, 1137, 1122, 1034 (CH$_n$—O—).

$^1$H NMR (200 MHz) [(8Z)-1,8-tetradecadien-4-yne] δ: 5.78 (ddt, J=22.5, 10.5, 2.2, 2.2 Hz, 1H, =CH -2), 5.54 (dd, J=22.5, 2.7 Hz, 1H, =CH$_2$-1a), 5.36 (dd, J=10.5, 2.2 MHz, 1H, CH$_2$-1b), 5.36 (dtt, J=11.0, 7.0, 7.0, 1.0, 1.0 Hz, 2H, CH=CH -8, 9), 2.31 (dt, J=2.1, 7.3, 7.3 Hz, 2H, CH$_2$-5), 2.15 (dt, J=7.0, 7.3, 7.3 Hz, 2H, CH$_2$-10), 2.03 (dt, J=6.4, 6.4, 6.7 Hz, 2H, CH$_2$-7), 1.59 (tt, J=7.0, 7.0, 8.0, 8.0 Hz, 2H, CH$_2$-6), 1.30 (m, 6H, CH$_2$-11, 12, 13), 0.89 (t, J=7.0 Hz, CH$_3$). $^{13}$C NMR (CDCl$_3$) [(8Z)-1,8-tetradecadien-4-yne] δ:

131.1 (=CH-9), 126.4 (=CH-8), 125.5 (=CH$_2$-1), 117.6 (=CH-2), 90.9 (≡C-4), 79.5 (≡C-3), 31.5 (CH$_2$-12), 29.4 (CH$_2$-10), 28.7 (CH$_2$-7), 27.2 (CH$_2$-11), 26.3 (CH$_2$-6), 22.6 (CH$_2$-5), 18.8 (CH$_2$-13), 14.1 (CH$_3$-14). MS [EI, m/z(%)] [(8Z)-1,8-tetradecadien-4-yne] 161 (M$^+$-29, 5), 133 (35), 119 (25), 105 (50), 91 (100), 79 (35), 67 (30), 41 (50). IR (CCl$_4$, cm$^{-1}$) [(8Z)-1,8-tetradecadien-4-yne] 3101 (=CH$_2$), 3009 (cis-=CH=CH and =CH$_2$), 2227, 2206 (acetylenic), 1833, 972, 913 (vinyl).

Example 17

Preparation of (Z)-8-tetradecen-4-ynol (19)

Tetrahydropyranyl ether 18, prepared in accordance with Example 16, was deprotected with Dowex™ 50W-X8 (Dow Chemical, Midland, Mich.) (40 mg) to form the alcohol 19 (107 mg, 56% yield based on the starting bromide 17). $^1$H NMR (200 MHz) δ: 5.35 (dtt, J=11.0, 7.0, 7.0, 1.0, 1.0 Hz, 2H, CH=CH -8,9), 3.68 (dt, J=6.5, 5.6, 5.6 Hz, 2H, CH$_2$-1), 2.44 (tt, J=6.5, 6.5, 2.5, 2.5 Hz, 2H, CH$_2$-2), 2.17 (tt, J=7.0, 7.0, 2.5, 2.5 Hz, 2H, CH$_2$-5), 2.12 (m, 2H, CH$_2$-7), 2.04 (m, 2H, CH$_2$-10), 1.76 (bt, J=6.5, 6.5 Hz, 1H, OH), 1.55 (tt, J=4×7.2 Hz, 2H, CH$_2$-6), 1.30 (m, 6H, CH$_2$-11, 12, 13), 0.89 (t, J=7.0 Hz, 3H, CH$_3$). MS [EI, m/z (%)] 179 (M$^+$-29, 8), 163 (21), 151 (15), 133 (53), 121 (38), 107 (87), 95 (66(, 93 (66), 91 (80), 81 (66), 79 (88), 67 (87), 55 (100), 41 (100), 29 (29). IR (CCl$_4$, cm$^{-1}$) 3636, 3588 (OH), 3006 (cis-CH=CH), 2227 (acetylenic), 1654 (C—O)

Example 18

Preparation of (3E,8Z)-3,8-tetradecadien-1-yl acetate (21)

(8Z)-Tetradecen-4-ynol (19) (21 mg, 0.1 mmol), prepared according to Example 17, was reduced with lithium tetrahydrialuminate (20 mg, 0.5 mmol) in dry diglyme (0.5 ml) at 120° C. for 3 hr. The alcohol (20) that was formed was acetylated with acetic anhydride (0.1 ml) and dry pyridine (0.5 ml), and the product was purified on silver-nitrate (20%) impregnated silica gel. This procedure afforded 18 mg (72% yield) of 21 having 97% isomeric purity. $^1$H NMR (500 MHz) δ: 5.51 (dtt, J=15.3, 6.8, 6.8, 1.2, 1.3 Hz, 1H, =CH -3), 5.38 (dtt, J=15.2, 6.6, 6.6, 1.2, 1.2 Hz, 1H, =CH -4), 5.35 (dtt J=11, 6.8, 6.8, 1.2, 1.2 Hz, 2H, CH=CH -8, 9), 4.07 (t, J=6.9, 6.9 Hz, 2H, CH$_2$-1), 2.31 (dtdt, J=3×6.8, 3×1.2 Hz, 2H, CH$_2$-2), 2.01 (tt, J=4×7.0 Hz, 6H, CH$_2$-5, 7, 10), 2.04 (s, 3H, COCH$_3$), 1.60–1.20 (8H, m, CH$_2$-6, 11, 12, 13), 0.88 (t, J=7.0, 7.0 Hz, 3H, CH$_3$). $^{13}$C NMR (125.7 MHz) δ: 171.1 (C=O), 133.3 (=CH-3), 130.3 and 129.4 (=CH-8, 9), 125.3 (=CH-4), 64.1 (CH$_2$-1); 32.2 (CH$_2$-2), 32.0 (CH$_2$-6), 31.5 (CH$_2$-12), 29.4 (CH$_2$-7, 10), 27.2 (CH$_2$-11), 26.6 (CH$_2$-5), 22.5 (CH$_2$-13), 21.0 (COCH$_3$), 14.1, (CH$_3$-14). MS [EI, m/z(%)], 252 (M$^+$, 0.5), 192 (M$^+$-60, 12), 163 (5), 138 (19), 124 (20), 121 (41), 107 (19), 95 (34, 93 (34), 82 (41, 80 (100, 79 (63, 67 (60), 55 (36), 43 (100), 41 (41). IR (CCl$_4$, cm$^{-1}$) 3006 (cis=C—H str), 1743 (=O), 1653 (CH=CH), 1403, 1238, 1035 (C—O), 969 (trans CH=CH wag). IR (gas phase, cm$^{-1}$) 3011 (cis=C—H str), 2934 (CH$_2$), 1761 (C=O), 1231, 1037 (—O—), 967 (trans CH=CH wag).

Example 19

Preparation of (3E,11Z)-3,11-tetradecadienyl acetate (30)

Starting from 1-butyne and 1-bromo-6-(tetrahydropyran-2-yloxy)-hexane (22), the (3E,11Z)-3,11-tetradecadien-1-yl acetate (30) was prepared by a synthetic route similar to that used for the preparation of (3E,8Z)-3,8-tetradecadien-1-yl acetate (21), as depicted in the following scheme.

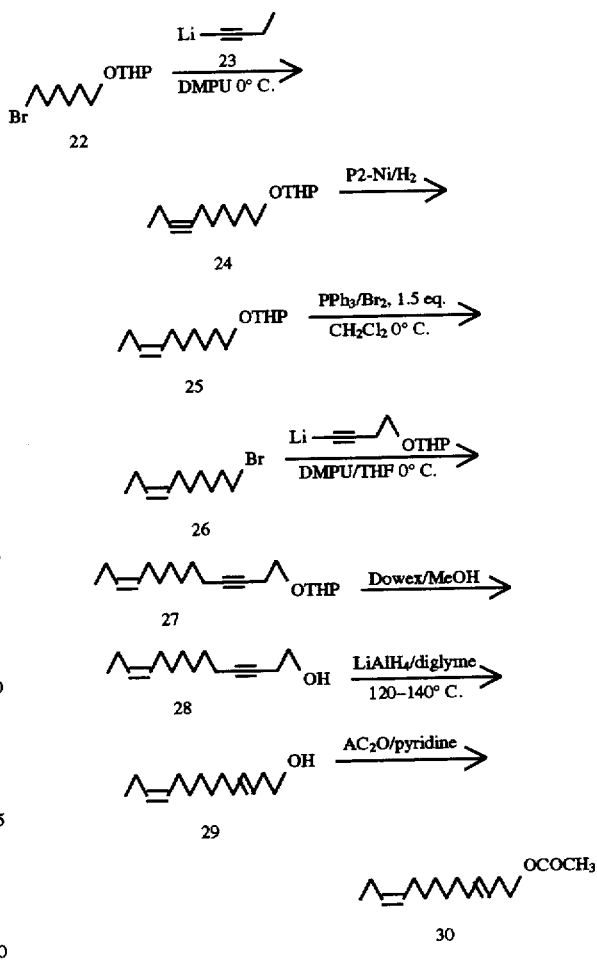

The yield was 15% [17 mg; 96% isomeric purity (GC)] based on the starting material, 1-bromo-6-(tetrahydropyran-2-yloxy)hexane (22). $^1$H NMR (500 MHz) δ: 5.51 (dtt, J=15.1, 6.8, 6.8, 1.2, 1.5 Hz, 1H, =CH -3), 5.35 (m, 3H, CH=CH -4, 11, 12), 4.06 (t, J=6.8, 6.8 Hz, 2H, CH$_2$-1), 2.31 (dddt, J=1.2, 1.2, 6.8, 6.8, 6.8 Hz, 2H, CH$_2$-2), 2.05 (s, 3H, COCH$_3$), 2.02 (m, 6H, CH$_2$-5, 10, 13), 1.36–1.24 (m, 6H, CH$_2$-6, 7, 8, 9), 0.95 (t, J=7.3, 7.6 Hz, 3H, CH$_3$). $^{13}$C NMR (100.6 MHz) δ: 171.1 (C=O), 133.6 (=CH-3), 131.6 (=CH-12), 129.3 (=CH-11), 125.0 (=CH-4), 64.1 (CH$_2$-1), 32.6 (CH$_2$-2), 31.9 (CH$_2$-6), 29.7 (CH$_2$-8), 29.3 (CH$_2$-7), 29.1 (CH$_2$-9), 29.0 (CH$_2$-10), 27.1 (CH$_2$-5), 21.0 (COCH$_3$), 20.5 (CH$_2$-13), 14.4 (CH$_3$-14). MS [EI, m/z(%)] 192 (M$^+$-60, 6), 163 (6), 149 (9), 135 (12), 121 (16), 107 (16), 96 (28), 95 (37), 93 (25), 82 (50), 81 (60), 80 (35), 79 (36), 69 (33) 68 (64), 67 (97), 55 (45), 43 (100), 41 (67). IR (CCl$_4$, cm$^{-1}$) 3006 (=CH cis str), 1743 (C=O), 1238, 1036 (C—O), 969 (=CH trans wag). IR (gas phase, cm$^{-1}$) 3012 (cis =C—H str), 2934 (CH$_2$), 1761 (C=O), 1231, 1038 (—O—), 968 (=CH trans wag).

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. An isolated 3,8,11-tetradecatrienyl acetate.
2. An isolated 3,8,11-tetradecatrienyl acetate according to claim 1, wherein said 3,8,11-tetradecatrienyl acetate is (3E,8Z,11Z)-3,8,11-tetradecatrienyl acetate.
3. An isolated 3,8,11-tetradecatrienyl acetate according to claim 1, wherein said 3,8,11-tetradecatrienyl acetate is substantially pure.
4. A composition comprising an isolated 3,8,11-tetradecatrienyl acetate and one or more compounds selected from the group consisting of a 3,8-tetradecadienyl acetate and a 3,11-tetradecadienyl acetate.
5. A composition according to claim 4, wherein the 3,8-tetradecadienyl acetate is (3E,8Z)-3,8-tetradecadienyl acetate and wherein the 3,11-tetradecadienyl acetate is (3E,11Z)-3,11-tetradecadienyl acetate.
6. A composition according to claim 4, wherein one of said compounds is (3E,8Z)-3,8-tetradecadienyl acetate.
7. A composition according to claim 4, wherein the 3,8,11-tetradecatrienyl acetate is (3E,8Z,11Z)-3,8,11-tetradecatrienyl acetate.
8. A moth trap comprising:
   a moth restraining member, and
   a moth attractant used in conjunction with said moth restraining member and comprising a 3,8,11-tetradecatrienyl acetate.
9. A moth trap according to claim 8, wherein said moth attractant further comprises one or more compounds selected from the group consisting of a 3,8-tetradecadienyl acetate and a 3,11-tetradecadienyl acetate.
10. A moth trap according to claim 9, wherein one of the compounds is (3E,8Z)-3,8-tetradecadienyl acetate.
11. A moth trap according to claim 8, wherein the 3,8,11-tetradecatrienyl acetate is (3E,8Z,11Z)-3,8,11-tetradecatrienyl acetate.
12. A moth trap according to claim 8, wherein said attractant is an isolated attractant.
13. A moth trap according to claim 12, wherein said isolated attractant is substantially pure.
14. A moth trap according to claim 8, wherein said moth restraining member is mechanical.
15. A moth trap according to claim 8, wherein said moth restraining member is adhesive.
16. A moth trap according to claim 8, further comprising an insecticide used in conjunction with said moth restraining member.
17. A moth trap according to claim 8, further comprising a dispenser which contains and sustainedly releases said moth attractant into the atmosphere.
18. A moth trap according to claim 17, wherein said dispenser is an attractant swellable polymeric capillary tube sealed at both ends.
19. A moth trap according to claim 17, wherein said attractant is admixed with an antioxidant.
20. A moth control composition comprising
    an insecticide and
    a moth attractant comprising a 3,8,11-tetradecatrienyl acetate.
21. A moth control composition according to claim 20, wherein said moth attractant further comprises one or more compounds selected from the group consisting of a 3,8-tetradecadienyl acetate and a 3,11-tetradecadienyl acetate.
22. A moth control composition according to claim 21, wherein one of the compounds is (3E,8Z)-3,8-tetradecadienyl acetate.
23. A moth control composition according to claim 20, wherein the 3,8,11-tetradecatrienyl acetate is (3E,8Z,11Z)-3,8,11-tetradecatrienyl acetate.
24. A moth control composition according to claim 20, wherein said insecticide is selected from the group consisting of: organophosphates, carbamates, pyrethroids, sulfluramids, and mixtures thereof.
25. A moth control composition according to claim 20, wherein said composition is placed on a support.
26. A moth control composition comprising:
    a biocontrol agent and
    a moth attractant comprising a 3,8,11-tetradecatrienyl acetate.
27. A moth control composition according to claim 26, wherein said moth attractant further comprises one or more compounds selected from the group consisting of a 3,8-tetradecadienyl acetate and a 3,11-tetradecadienyl acetate.
28. A moth control composition according to claim 27, wherein one of the compounds is (3E,8Z)-3,8-tetradecadienyl acetate.
29. A moth control composition according to claim 26, wherein the 3,8,11-tetradecatrienyl acetate is (3E,8Z,11Z)-3,8,11-tetradecatrienyl acetate.
30. A moth control composition according to claim 26, wherein said biocontrol agent is selected from the group consisting of pathogenic nematodes, fungi, yeast, bacteria, and viruses.
31. A moth control composition according to claim 26, wherein said composition is placed on a support.
32. A method of attracting moths to a particular location comprising:
    providing at the particular location about 10 picograms to about 10 milligrams of a moth attractant comprising a 3,8,11-tetradecatrienyl acetate.
33. A method according to claim 32, wherein the moth attractant further comprises one or more compounds selected from the group consisting of a 3,8-tetradecadienyl acetate and a 3,11-tetradecadienyl acetate.
34. A method according to claim 33, wherein one of the compounds is (3E,8Z)-3,8-tetradecadienyl acetate.
35. A method according to claim 32, wherein the 3,8,11-tetradecatrienyl acetate is (3E,8Z,11Z)-3,8,11-tetradecatrienyl acetate.
36. A method according to claim 32, wherein the moths are *Scrobipalpuloides absoluta*.
37. A method for controlling a population of moths comprising:
    attracting moths to a particular location with about 10 picograms to about 10 milligrams of a moth attractant comprising a 3,8,11-tetradecatrienyl acetate and
    exposing the moths, proximate to the particular location, to an agent which impairs the moths' ability to mate.
38. A method according to claim wherein the moth attractant further comprises one or more compounds selected from the group consisting of a 3,8-tetradecadienyl acetate and a 3,11-tetradecadienyl acetate.
39. A method according to claim 38, wherein one of the compounds is (3E,8Z)-3,8-tetradecadienyl acetate.
40. A method according to claim 37, wherein the 3,8,11-tetradecatrienyl acetate is (3E,8Z,11Z)-3,8,11-tetradecatrienyl acetate.
41. A method according to claim 37, wherein the moths are *Scrobipalpuloides absoluta*.
42. A method according to claim 37, wherein the agent is a restraining device.
43. A method according to claim 42, wherein the restraining device is a mechanical restraint.
44. A method according to claim 42, wherein the restraining device is an adhesive.

45. A method according to claim 37, wherein the agent is an insecticide.

46. A method according to claim 45, wherein the insecticide is selected from the group consisting of: organophosphates, carbamates, pyrethroids, sulfluramids, and mixtures thereof.

47. A method according to claim 37, wherein the agent is a biocontrol agent.

48. A method according to claim 47, wherein the biocontrol agent is selected from the group consisting of pathogenic nematodes, fungi, yeast, bacteria, and viruses.

49. A method of disrupting mating of moths in a particular area comprising:

provifing in the particular area a quantity of an attractant above that emanating from moths and comprising a 3,8,11-tetradecatrienyl acetate in a quantity sufficient to prevent pheromone communication.

50. A method according to claim 49, wherein the attractant further comprises one or more compounds selected from the group consisting of a 3,8-tetradecadienyl acetate and a 3,11-tetradecadienyl acetate.

51. A method according to claim 50, wherein one of the compounds is (3E,8Z)-3,8-tetradecadienyl acetate.

52. A method according to claim 49, wherein the 3,8,11-tetradecatrienyl acetate is (3E,8Z,11Z)-3,8,11-tetradecatrienyl acetate.

53. A method according to claim 49, wherein the moths are *Scrobipalpuloides absoluta*.

54. A method of synthesizing (3E,8Z,11Z)-3,8,11-tetradecatrienyl acetate, comprising:

providing a trienyl alcohol having the formula:

and acetylating the alcohol.

55. A method according to claim 54, wherein said providing a trienyl alcohol comprises:

providing a dieneynyl alcohol having the formula:

and reducing the dieneynyl alcohol to form a trienyl alcohol.

56. A method according to claim 55, wherein said providing an dieneynyl alcohol comprises:

providing a dienyl halide having the formula:

wherein X is a halogen atom, alkylating the dienyl halide with an alkali metal salt of a protected 3-butynol, thereby forming a protected dieneynyl alcohol having the formula:

wherein Y is an alcohol protecting group, and deprotecting the protected dieneynyl alcohol.

57. A method according to claim 56, wherein said providing a dienyl halide comprises:

providing a protected acetylene having the formula:

wherein Z is an alcohol protecting group;

Grignard coupling the protected acetylene with pentynyl tosylate, thereby forming a diyne having the formula:

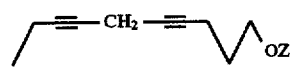

hydroborating the diyne to form a vinylborane;

hydrolyzing the vinyl borane to form a vinylborate;

oxidizing the vinylborate to form a protected dienyl alcohol; and converting the protected dienyl alcohol into the dienyl halide.

58. A trienyl alcohol having the formula:

59. A dieneynyl alcohol having the formula:

60. A protected dieneynyl alcohol having the formula:

wherein Y is an alcohol protecting group.

61. A dienyl halide having the formula:

wherein X is a halogen atom.

62. A composition according to claim 4, wherein said composition comprises about 90% by weight of the 3,8,11-tetradecatrienyl acetate.

* * * * *